(12) United States Patent
O'Brien et al.

(10) Patent No.: US 6,350,885 B1
(45) Date of Patent: Feb. 26, 2002

(54) TRICYCLIC HETEROAROMATICS AND THEIR DERIVATIVES AS INHIBITORS OF MATRIX METALLOPROTEINASES

(75) Inventors: Patrick Michael O'Brien, Stockbridge; Joseph Armand Picard, Canton; Drago Robert Sliskovic, Saline, all of MI (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 09/719,026

(22) PCT Filed: Jun. 2, 1999

(86) PCT No.: PCT/US99/12272

§ 371 Date: Feb. 20, 2001

§ 102(e) Date: Feb. 20, 2001

(87) PCT Pub. No.: WO00/06560

PCT Pub. Date: Feb. 10, 2000

Related U.S. Application Data

(60) Provisional application No. 60/094,705, filed on Jul. 30, 1998.

(51) Int. Cl.$^7$ .................. C07D 307/91; A61K 31/38; A61K 31/343

(52) U.S. Cl. .................. 549/460; 549/461; 514/468; 514/443

(58) Field of Search .................. 514/443, 468; 549/460, 461

(56) References Cited

U.S. PATENT DOCUMENTS 5,627,206 A * 5/1997 Hupe et al. .................. 514/468

FOREIGN PATENT DOCUMENTS

| DE | 2 033 959 | 2/1971 |
|---|---|---|
| EP | 0 555 824 A1 | 8/1993 |
| WO | WO 96/38434 | 12/1996 |
| WO | WO 98/06711 | 2/1998 |
| WO | WO 98/09934 | 3/1998 |
| WO | WO 98/09957 | 3/1998 |
| WO | WO 98/16503 | 4/1998 |

OTHER PUBLICATIONS

.P. Cagniant et al.:Bull.De La Soc. Chim. De Fr., 12,4435–42(1971):XP002116957.*

T. Keumi et al.:Seni Kogyo Kenyu Shisetsu Hokoku, 14, 71–7(1976); also cited as HCAPLUS–1978:152329.*

Aisen P.S., "Anti–inflammatory therapy for Alzheimer's disease", *Neurobiology of Aging*, vol. 21, pp. 447–448 (2000).

Andersen, K. et al., "Do nonsteroidal anti–inflammatory drugs decrease the risk for Alzheimer's disease? The Rotterdam Study", *Neurology*, vol. 45, pp. 1441–1445 (Aug. 1995).

Andrews, H.J. et al., "A synthetic peptide metalloproteinase inhibitor, but not Timp, prevents the breakdown of proteoglycan within articular cartilage in vitro", *Agents Actions*, vol. 37, pp. 147–157 (1992).

Armstrong, P.W. et al., "Structural remodeling in heart failure: gelatinase induction", *Can. J. Cardiol.*, vol. 10, No. 2, pp. 214–220 (Mar. 1994).

Bagchus, W.M. et al., "Glomerulonephritis Induced by Monoclonal Anti–Thy 1.1 Antibodies: A Sequential Histological and Ultrastructural Study in the Rate", *Laboratory Investigation*, vol. 55, No. 6, pp. 680–687 (1986).

Bendeck, M.P. et al., "Smooth muscle cell migration and matrix metalloproteinase expression after arterial injury in the rat", *Circulation Research*, vol. 75, No. 3, pp. 539–545 (Sep. 1994).

Benelli, R. et al., "Inhibition of AIDS–Kaposi's Sarcoma Cell Induced Endothelial Cell Invasion by TIMP–2 and a Synthetic Peptide from the Metalloproteinase Propeptide: Implications for an Anti–Angiogenic Therapy", *Oncology Research*, vol. 6, No. 6, pp. 251–257 (1994).

Breitner, J.C.S. et al., "Inverse association of anti–inflammatory treatments and Alzheimer's disease: Initial results of a co–twin control study", *Neurology*, 44: 227–232 (Feb. 1994).

Breitner, J.C.S. et al., "Delayed onset of Alzheimer's disease with nonsteroidal anti–inflammatory and histamine H2 blocking drugs", *Neurobiol. Aging*, vol. 16, No. 4, pp. 523–530 (1995).

Brown, P. et al., "Independent Expression and Cellular Processing of $M_r$ 72,000 Type IV Collagenase and Interstitial Collagenase in Human Tumorigenic Cell Lines", *Cancer Research*, vol. 50, pp. 6184–6191 (Oct. 1, 1990).

Brown, S.I. et al., "Collagenolytic activity of alkali burned corneas", *Arch. Ophthalmol.*, vol. 81, pp. 370–373 (Mar. 1969).

(List continued on next page.)

*Primary Examiner*—Richard L. Raymond
*Assistant Examiner*—Sudhaker B. Patel
(74) *Attorney, Agent, or Firm*—Merchant & Gould P.C.

(57) ABSTRACT

Tricyclic heteroaromatic compounds and derivatives are described as well as methods for the preparation and pharmaceutical compositions of same, which are useful as inhibitors of matrix metalloproteinases, particularly gelatinase A, collagenase-3, and stromelysin-1 and for the treatment of multiple sclerosis, atherosclerotic plaque rupture, aortic aneurysm, heart failure, left ventricular dilation, restenosis, periodontal disease, corneal ulceration, treatment of burns, decubital ulcers, wound healing, cancer, inflammation, pain, arthritis, osteoporosis, renal disease, or other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

28 Claims, No Drawings

OTHER PUBLICATIONS

Burns, F. et al., *Invest. Ophthalmol.*, vol. 30, No. 7, pp. 1569–1575 (Jul. 1989).

"The Canadian Study of helath and Aging: Risk factors for Alzheimer's disease in Canada", *Neurology*, vol. 44, pp. 2073–2080 (Nov. 1994).

Clark, R.K. et al., "Development of tissue damage, inflammation and resolution following stroke: an immunohistochemical and quantitative planimetric study", *Brain Research Bulletin*, vol. 31, pp. 565–572 (1993).

Davies, B. et al., et al., "A synthetic Matrix Metalloproteinase Inhibitor Decreases Tumor Burden and Prolongs Survival of Mice Bearing Human Ovarian Carcinoma Xenografts", *Cancer Reasearch*, vol. 53, pp. 2087–2091 (May 1, 1993).

Davies, M. et al., "Proteinases and glomerular matrix turnover", *Kidney International*, vol. 41, pp. 671–678 (1992).

DeClerck, Y. et al., "Inhibition of Invasion and Metastasis in Cells Transfected with an Inhibitor of Metalloproteinases", *Cancer Res.*, vol. 52, pp. 701–708 (Feb. 1, 1992).

Ellis, A.J. et al, "The Prevention of Collagen Breakdown in Bovine Nasal Cartilage by TIMP, TIMP–2 and a Low Molecular Weight Synthetic Inhibitor", *Biochemical and Biophysical Research Communications*, vol. 201, No. 1, pp. 94–101 (May 30, 1994).

Freije, José et al., *Journal of BiologicalChemistry*, vol. 269, No. 24, pp. 16766–16773 (1994).

Galis, Z. et al, "Increased expression of matrix metalloproteinases and matrix degrading activity in vulnerable regions of human atherosclerotic plaques", *J. Clin. Invest.*, vol. 94, pp. 2493–2503 (Dec. 1994).

Gendelman, H. et al., "Macrophages/microglia and the pathoophysiology of CNS injuries in AIDS", *Journal of Leukocyte Biology*, vol. 56, pp. 387–388 (Sep. 1994).

Gijbels, K. et al., *J. Clin. Invest.*, vol. 94, pp. 2177–2182 (Dec. 1994).

Giulian D. et al., "Inflammatory glia mediate delayed neuronal damage after ischemia in the central nervous system", *Inflammatory Neurotoxins and Stroke/Supplement I Stroke*, vol. 24, No. 12, pp. 184–190 (Dec. 1993).

Grams, F. et al., "X–ray structures of human neutrophil collagenase complexed with peptidie hydroxamate and peptide thiol inhibitors: Implications for substrate binding and rational drug design", *Eur. J. Biochem*, vol. 228, pp. 830–841 (1995).

Hampel, H. et al., "Inflammatory and Immunological Mechanisms in Alzheimer's Disease", *DN&P*, vol. 8, No. 10, pp. 599–608 (Dec. 1995).

Henney A. et al., "Localization of stromelysin gene expression in atherosclerotic plaques by in situ hybridization", *Proc. Nat'l. Acad. Sci.*, vol. 88, pp. 8154–8158 (Sep. 1991).

Kitamura, M. et al. "Gene transfer of metalloproteinase transin induces aberrant behavior of cultured mesangial cells", *International Society of Nephrology*, vol. 45, pp. 580–1586 (1994).

Lee, T. et al., "Impact of Left VentricULAR Size on the Survival in Advanced Heart Failure", *Am. J. Cardiol.*, vol. 72, pp. 672–676 (Sep. 5, 1993).

Leigh P.N., "Pathogenic Mechanisms in Amyotrophic Lateral Sclerosis and Other Motor Neuron Disorders", *Neurodegenerative Diseases*, W.B. Saunders Company, Chapter 28, pp. 473–478 (1994).

Lovett, D. et al., "Structural Characterization of the Mesangial Cell Type IV Collagenase and Enhanced Expression in a Model of Immune Complex–mediated Glomerulonephritis", *American J. of Pathology*, vol. 141, No. 1, pp. 85–98 (Jul. 1992).

Lucca, U. et al., "Nonsteroidal Antiinflammatory Drug Use in Alzheimer's Disease", *Society of Biological psychiatry*, vol. 36, pp. 854–866 (1994).

Mandybur T.I., et al. "Cerebral Amyoid Angiopathy With Granulomatous Angiitis Ameliorated by Steroidi–Cytoxan Treatment", *Clin. Neuropharm.*, vol. 15, No. 3, pp. 241–247 (1992).

Marti, H. et al., "Homology cloning of rat 72 kDa type IV collagenase: cytokine and second–messenger inducibility in glomerular mesangial cells", *Biochem. J.*, vol. 291, pp. 441–446 (1993).

Marti, H.P. et al., "Transforming Growth Factor–β1 Stimulates Glomerular Mesangial Cell Synthesis of the 72–kd Type IV Collagenase", *American Journal of Pathology*, vol. 144, No. 1, pp. 82–94 (Jan., 1994).

Martin, J. et al., "Enhancement of Glomerular Mesangial Cell Neutral Proteinase Secretion by Macrophages: role of Interleukin", *Journal of Immunology*, vol. 137, No. 2, pp. 525–529 (Jul. 15, 1986).

Martin R. et al., "Immunological Aspects of Demyelinating Diseases", *Annul Rev. Immunol.*, vol. 10, pp. 153–187 (1992).

Martin, R. et al., "Immunological Aspects of Experimental Allergic Encephalomyelitis and Multiple Sclerosis", *Critical Review in Clinical Laboratory Sciences*, vol. 32, No. 2, pp. 121–182 (1992).

McGeer, E., "Neurodegeneration and the Immune System", In: *Neurodegenerative Diseases*, W.B. Saunders, Chapter 18, pp. 277–300 (1994).

McGeer, P. et al., "Anti–inflammatory agents as a therapeutic approach to Alzheimer's disease", *Neurology*, vol. 42, pp. 447–449 (Feb., 1992).

McGeer, P. et al., Neuroimmune Mechanisms in Alzheimer Disease Pathogenesis, *Alzheimer Disease and Associated Disorders*, vol. 8, No. 3, pp. 149–158 (1994).

Melchiori, A. et al.,"Inhibition of Tumor Cell Invasion by a Highly Conserved Peptide Sequence from the Matrix Metalloproteinase Enzyme Prosegment", *Cancer Res.*, vol. 52, pp. 2353–2356 (Apr. 15, 1992).

Monsky, W. et al., "Binding and Localization of $M_r$ 72,000 Matrix Metalloproteinase at Cell Surface Invadopodia", *Cancer Research*, vol. 53, pp. 3159–3164 (1993).

Overall, C.M. et al., "Demonstrations of tissue collagenase activity in vivo and its relationship to inflammation severity in human gingiva", *Journal of Periodontal Research*, vol. 22, pp. 81–88 (1987).

Patterson, P., "Cytokines in Alzheimer's disease and multiple sclerosis", *Current Opinion in Neurobiology*, vol. 5, pp. 642–656 (1995).

Pauly, R. et al., "Migration of Cultured Vascular Smooth Muscle Cells Through a Basement Membrane Barrier Requires Type IV Collagenase Activity and Is Inhibited by Cellular Differentiation", *Circulation Research*, vol. 75, No. 1, pp. 41–54 (Jul. 1994).

Reddy, H.K. et al., [Abstract] "Activated myocardial collagenase in idiopathic dilated cardiomyopathy: A marker of dilation and remoldeling", *Clinical Research*, vol. 41, No. 3, p. 660A (1993).

Rich, J.B. et al., "Nonsteroidal anti–inflammatory drugs in Alzheimer's disease", *Neurology*, vol. 45, pp. 51–55 (1995).

Rogers, J. et al., "Inflammation and Alzheimer's Disease Pathogenesis", *Neurobiology of Aging*, vol. 17, No. 5, pp. 681–686 (1986).

Romanic, A. et al., "The Induction of 72–kDa Gelatinase in T Cells upon Adhesion to Endothelial Cells is VCAM–1 Dependent", *The Journal of Cell Biology*, vol. 125, pp. 1165–1178 (Jun. 1994).

Rotherwell, N.J. et al., "Involvement of Cytokines in Acute Neurodegeneration in the CNS", *Neuroscience and Biobehavioral Reviews*, vol. 17, pp. 217–227 (1993).

Saarialho–Kere, U. et al., "Distinct Populations of Basal Keratinocytes Express Stromelysin–1 and Stromelysin–2 in Chronic Wounds", *J. Clin. Invest.*, vol. 94, pp. 79–88 (Jul. 1994).

Sabbah, H. et al, "Left ventricular shape changes during the course of evolving heart failure", *The American Physiological Society*, vol. 263, pp. H266–H270 (1992).

Strongin, A. et al., "Plasma Membrane–dependent Activation of the 72–kDa Type IV Collagenase Is Prevented by Complex Formation with TIME–2", *The Journal of Biological Chemistry*, vol. 268, No. 19, pp. 14033–14039 (Jul. 5, 1993).

Taraboletti, G. et al., "Inhibition of Angiogenesis and Murine Hemangioma Growth by Batimastat, a Synthetic Inhibitor of Matrix Metalloproteinases", *Journal of the National Cancer Institute* vol. 87, No. 4, pp. 293–298 (Feb. 15, 1995).

Turck, J. et al., "Matrix Metalloproteinase 2 (Gelatinase A) Regulates Glomerular Mesangial Cell Proliferation and Differentiation", *The Journal of Biological Chemistry*, vol. 271, No. 25, pp. 15074–15083 (Jun. 21, 1996).

Uitto, V.J. et al., "Collagenase and neutral metalloproteinase activity in extracts from inflamed human gingival", *Journal of Periodontal Research*, vol. 16, pp. 417–424 (1981).

Vincenti, M. et al., "Using Inhibitors of Metalloproteinases to Treat Arthritis", *Arthritis & Rheumatism*, vol. 37, No. 8, pp. 1115–1126 (Aug. 1994).

Vine, N. et al., "Metalloproteinases in degenerative aortic diseases", *Clinical Science* vol. 81, pp. 233–239 (1991).

Walakovits, L. et al., "Detection of Stromelysin and Collagenase in Synovial Fluid from Patients with Rheumatoid Arthritis and Posttraumatic Knee Injury", *Arthritis and Rheumatism*, vol. 35, No. 1, pp. 35–42 (Jan. 1992).

Woessner Jr., J. "Matrixi metalloproteinases and their inhibitors in connective tissue remodeling", *The FASEB Journal*, vol. 5, pp. 2145–2154 (May 1991).

Zafarullah, M. et al., "Elevated Metalloproteinases and Tissue Inhibitor of Metalloproteinase mRNA in Human Osteoarthritic Synovia", *The Journal of Rheumatology*, vol. 20, No. 4, pp. 693–697 (1993).

P. Cagniant et al., "Etude de la succinoylation et de la glutaroylation du tetrahydro–1,2,3,4 dibenzofuranne; nouvelle synthese du β–brazane" *Bulletin De La Societe Chimique De France*, No. 12, pp. 4435–4442.

T. Keumi et al., Chemical Abstracts, vol. 88, No. 21, Abstract No. 152329u, p. 581.

* cited by examiner

TRICYCLIC HETEROAROMATICS AND THEIR DERIVATIVES AS INHIBITORS OF MATRIX METALLOPROTEINASES

CROSS-REFERENCE TO RELATED APPLICATION

The instant application is a 371 application of PCT/US99/12272 filed Jun. 2, 1999 which claims the benefit of provisional application 60/094,705, filed Jul. 30, 1998.

BACKGROUND OF THE INVENTION

The present invention relates to novel tricyclic heteroaromatic compounds and their derivatives useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (MMP-2), collagenase-3 (MMP-13), and stromelysin-1 (MMP-3). More particularly, the novel compounds of the present invention are useful in the treatment of atherosclerotic plaque rupture, aortic aneurism, heart failure, left ventricular dilation, restenosis, periodontal disease, corneal ulceration, treatment of burns, decubital ulcers, wound repair, cancer, inflammation, pain, arthritis, osteoporosis, multiple sclerosis, renal disease, and other autoimmune or inflammatory disorders dependent on the tissue invasion of leukocytes or other activated migrating cells. Additionally, the compounds of the present invention are useful in the treatment of acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

Gelatinase A and stromelysin-1 are members of the matrix metalloproteinase (MP) family (Woessner J. F., *FASEB J.*, 1991;5:2145–2154). Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C.,*J. Biol. Chem.*, 1994;269:16766–16773), and the newly discovered membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is a focal point for inhibitor design. The modification of substrates by introducing chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of an atherosclerotic plaque is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-l, and interstitial collagenase. In situ zymography of this tissue revealed increased gelatinolytic and caseinolytic activity (Galis Z. S., Sukhova G. K., Lark M. W., and Libby P., "Increased expression of matrix metalloproteinases and matrix degrading activity in vulnerable regions of human atherosclerotic plaques," *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization," *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases," *Clin. Sci.*, 1991;81:233–239).

Heart failure arises from a number of diverse etiologies, but a common characteristic is cardiac dilation, which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure," *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy," *Clin. Res.*, 1993;41:660A; Tyagi S. C., Reddy H. K., Voelker D., Tjara I. E., and Weber K. T., "Myocardial collagenase in failing human heart," *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction," *Can. J. Cardiol.*, 1994; 10:214–220), and cardiac dilation precedes profound deficits in cardiac function (Sabbah H. N., Kono T., Stein P. D., Mancini G. B., and Goldstein S., "Left ventricular shape changes during the course of evolving heart failure," *Am. J. Physiol.*, 1992;263:H266–270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat,"*Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R, Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation," *Circulation Research*, 1994;75:41–54).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva," J. Periodontal Res., 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva," J. Periodontal Res., 1987;22:81–88). Proteolytic degradation of extracellular matrix has been observed in corneal ulceration following alkali burns (Brown S. I., Weller C. A., and Wasserman H. E., "Collagenolytic activity of alkali burned corneas," Arch. Ophthalmol., 1969;81:370–373). Thiol-containing peptides inhibit the collagenase isolated from alkali-burned rabbit corneas (Burns F. R., Stack M. S., Gray R. D., and Paterson C. A., Invest. Ophthalmol., 1989;30:1569–1575).

Stromelysin is produced by basal keratinocytes in a variety of chronic ulcers (Saarialho-Kere U. K., Ulpu K., Pentland A. P., Birkedal-Hansen H., Parks W. O., and Welgus H. G., "Distinct Populations of Basal Keratinocytes Express Stromelysin-1 and Stromelysin-2 in Chronic Wounds," J. Clin. Invest., 1994;94:79–88).

Stromelysin-1 mRNA and protein were detected in basal keratinocytes adjacent to but distal from the wound edge in what probably represents the sites of the proliferating epidermis. Stromelysin-1 may thus prevent the epidermis from healing.

Davies et al., (Cancer Res., 1993;53:2087–2091) reported that a peptide hydroxamate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., Cancer Res., 1992;52:2353–2356). The natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., Cancer Res., 1992;52:701–708). Studies of human cancers have shown that gelatinase A is activated on the invasive tumor cell surface (Strongin A. Y., Marner B. L., Grant G. A., and Goldberg G. I., J. BioL Chem., 1993;268:14033–14039) and is retained there through interaction with a receptor-like molecule (Monsky W. L., Kelly T., Lin C.-Y., Yeh Y., Stetler-Stevenson W. G., Mueller S. C., and Chen W.-T., Cancer Res., 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., Journal of the National Cancer Institute, 1995;87:293 and Benelli R., Adatia R., Ensoli B., Stetler-Stevenson W. G., Santi L., and Albini A, Oncology Research, 1994;6:251–257).

Several investigators have demonstrated consistent elevation of stromelysin and collagenase in synovial fluids from osteo- and rheumatoid arthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury," Arthritis Rheum., 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia," J. Rheumatol., 1993;20:693–697). TIKP-1 and TIMP-2 prevented the formation of collagen fragments, but not proteoglycan fragments in both the bovine nasal and pig articular cartilage models for arthritis, while a synthetic peptide hydroxamate could prevent the formation of both fragments (Andrews H. J., Plumpton T. A., Harper G. P., and Cawston T. E., Agents Actions, 1992;37: 147–154; Ellis A. J., Curry V. A., Powell E. K., and Cawston T. E., Biochem. Biophys. Res. Commun., 1994;201:94–101).

Gijbels et al., (J. Clin. Invest., 1994;94:2177–2182) recently described a peptide hydroxamate, GM6001, that suppressed the development or reversed the clinical expression of experimental autoimmune encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M., and Madri J. A., "The Induction of 72-kDa Gelatinase in T Cells upon Adhesion to Endothelial Cells is VCAM-1 Dependent," J. Cell Biology, 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Also, leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective inhibitor of gelatinase A and/or stromelysin- I would have value in the treatment of diseases involving disruption of extracellular matrix resulting in inflammation due to lymphocytic infiltration, inappropriate migration of metastatic or activated cells, or loss of structural integrity necessary for organ function.

Neuroinflammatory mechanisms are implicated in a broad range of acute and chronic neurodegenerative disorders, including stroke, head trauma, multiple sclerosis, and Alzheimer's disease, to name a few (McGeer E. G. and McGeer P. L., "Neurodegeneration and the immune system". In: Calne D. B., ed. Neurodegenerative Diseases, W. B. Saunders, 1994:277–300). Other disorders that may involve neuroinflammatory mechanisms include amyotrophic lateral sclerosis (Leigh P. N., "Pathogenic mechanisms in amyotrophic lateral sclerosis and other motor neuron disorders". In: Calne D. B., ed., Neurodegenerative Diseases, W. B. Saunders, 1994:473–88), cerebral amyloid angiopathy (Mandybur T. I. and Balko G., "Cerebral amyloid angiopathy with granulomatous angiitis ameliorated by steroid-cytoxan treatment," Clin. Neuropharm., 1992;15:241–7), AIDS (Gendelman H. E. and Tardieu M., "Macrophages/microglia and the pathophysiology of CNS injuries in AIDS," J. Leukocyte Biol., 1994;56:387–8), Parkinson's disease, Huntington's disease, prion diseases, and certain disorders involving the peripheral nervous system, such as myasthenia gravis and Duchenne's muscular dystrophy. Neuroinflammation, which occurs in response to brain injury or autoimmune disorders, has been shown to cause destruction of healthy tissue (Martin R., MacFarland H. F., and McFarlin D. E., "Immunological aspects of demyelinating diseases," Annul Rev. Immunol., 1992; 1 0:153–87; Clark R. K., Lee E. V., Fish C. J., et al., "Development of tissue damage, inflammation and resolution following stroke: an immunohistochemical and quantitative planimetric study," *Brain Res. Bull.*, 1993;31:565–72; Giulian D. and Vaca K., "Inflammatory glia mediate delayed neuronal damage after ischemia in the central nervous system," *Stroke*, 1993;24(Suppl 12):184–90; Patterson P. H., "Cytokines in Alzheimer's disease and multiple sclerosis," *Cur. Opinion Neurobiol.*, 1995;5:642–6; McGeer P. L., Rogers J., and McGeer E. G., "Neuroimmune mechanisms in Alzheimer disease pathogenesis," *Alzheimer Dis. Assoc. Disorders*, 1994;8:149–58; Martin R. and McFarland H. F., "Immunological aspects of experimental allergic encephalomyelitis and multiple sclerosis," *Crit. Rev. Clin. Lab. Sci*, 1995;32:121–82; Rogers J., Webster S., Lue L. F., et al., "inflammation and Alzheimer's disease pathogenesis". In: *Neurobiology of Aging*, 1996;17:681–686; Rothwell N. J. and Relton J. K., "Involvement of cytokines in acute neurodegeneration in the CNS," *Neurosci Biobehav. Rev.*, 1993;17:217–27). The pathological profiles and clinical courses of these disorders differ widely, but they all have in common the participation of immune/inflammatory elements in the disease process. In particular, many neurodegenerative disorders are characterized by large numbers of reactive microglia in postmortem brain samples, indicative of an active inflammatory process (McGeer E. G. and McGeer P. L., supra., 1994).

Increasing attention is being directed toward inflammatory mechanisms in Alzheimer's disease. Several lines of evidence support the involvement of neuroinflammation in Alzheimer's disease: 1) There is a significant increase in inflammatory markers in the Alzheimer brain, including acute phase reactants, cytokines, complement proteins, and MHC molecules (McGeer et al., supra., 1994; Rogers et al., supra.); 2) There is evidence that β-amyloid induces neurodegenerative changes primarily through interactions with inflammatory molecules, and that inflammation alone is sufficient to induce neurodegeneration (Rogers et al., supra); and 3) Growing epidemiological data indicate that anti-inflammatory therapy can delay the onset and slow the progression of Alzheimer's disease (McGeer P. L. and Rogers J., "Anti-inflammatory agents as a therapeutic approach to Alzheimer's disease," *Neurology*, 1992;42:447–9; Canadian Study of Health and Aging, "Risk factors for Alzheimer's disease in Canada," *Neurology*, 1994;44:2073–80; Lucca U., Tettamanti M., Forloni G., and Spagnoli A., "Nonsteroidal antiinflammatory drug use in Alzheimer's disease," *Biol. Psychiatry*, 1994;36:854–66; Hampel H. and Müller N., "inflammatory and immunological mechanisms in Alzheimer's disease," *DN&P*, 1995;8:599–608; Breitner J. C. S., Gau B. A., Welsh K. A., et al., "Inverse association of anti-inflammatory treatments and Alzheimer's disease: Initial results of a co-twin control study," *Neurology*, 1994;44:227–32; Breitner J. C. S., Welsh K. A., Helms M. J., et al., "Delayed onset of Alzheimer's disease with nonsteroidal anti-inflammatory and histamine H2 blocking drugs," *Neurobiol. Aging*, 1995;16:523–30; Andersen K., Launer L. J., Ott A., Hoes A. W., Breteler M. M. B., and Hofman A., "Do nonsteroidal anti-inflammatory drugs decrease the risk for Alzheimer's disease? The Rotterdam Study," *Neurology*, 1995;45:1441–5; Rich J. B., Rasmusson D. X., Folstein M. F., et al., "Nonsteroidal anti-inflammatory drugs in Alzheimer's disease," *Neurology*, 1995;45:51–5; Aisen P. S., "Anti-inflammatory therapy for Alzheimer's disease," *Dementia*, 1995;9:173–82; Rogers et al., supra). Chronic use of non-steroidal anti-inflammatory drugs (NSAIDs), most commonly for the treatment of rheumatoid arthritis, decreases the probability of developing Alzheimer's disease, and there is reason to believe that other anti-inflammatory agents may also be effective, although direct evidence for the efficacy of such treatments is lacking (Hamper and Müller, supra., 1995). Furthermore, virtually all of the currently available compounds, which include corticosteroids, NSAIDs, antimalarial drugs, and colchicine, have serious drawbacks that make them undesirable in the treatment of chronic disorders. Glucocorticoids, which are in wide clinical use as anti-inflammatory/immunosuppressive drugs, can be directly neurotoxic and also are toxic to systemic organs at moderate to high doses. NSAIDs have gastrointestinal and renal side effects that obviate long-term use in most people, and few of them cross the blood-brain barrier in significant amounts. The toxic properties of chloroquine compounds and colchicine also are well known. An anti-inflammatory drug that is well-tolerated by patients and that crosses the blood-brain barrier has significant advantages for the treatment of acute and chronic degenerative diseases of the central nervous system.

Normal kidney function is dependent on the maintenance of tissues constructed from differentiated and highly specialized renal cells which are in a dynamic balance with their surrounding extracellular matrix (ECM) components (Davies M. et al., "Proteinases and glomerular matrix turnover," *Kidney Int.*, 1992;41:671–678). Effective glomerular filtration requires that a semi-permeable glomerular basement membrane (GBM) composed of collagens, fibronectin, enactin, laminin and proteoglycans is maintained. A structural equilibrium is achieved by balancing the continued deposition of ECM proteins with their degradation by specific metalloproteinases (MMP). The MMP belong to a supergene family of zinc endopeptidases (Woessner J. F., "Matrix metalloproteinases and their inhibitors in connective tissue remodelling,"*FASEB J.*, 1991;5:2145–2154). These proteins are first secreted as proenzymes and are subsequently activated in the extracellular space. These proteinases are in turn subject to counter balancing regulation of their activity by naturally occurring inhibitors referred to as TIMPs (tissue inhibitors of metalloproteinases).

Deficiency or defects in any component of the filtration barrier may have catastrophic consequences for longer term renal function. For example, in hereditary nephritis of Alport's type, associated with mutations in genes encoding ECM proteins, defects in collagen assembly lead to progressive renal failure associated with splitting of the GBM and eventual glomerular and interstitial fibrosis. By contrast in inflammatory renal diseases such as glomerulonephritis, cellular proliferation of components of the glomerulus often precede obvious ultrastructural alteration of the ECM matrix. Cytokines and growth factors implicated in proliferative glomerulonephritis such as interleukin-1, tumor necrosis factor, and transforming growth factor beta can upregulate metalloproteinase expression in renal mesangial cells (Martin J. et al., "Enhancement of glomerular mesangial cell neutral proteinase secretion by macrophages: role of interleukin 1," *J. Immunol.*, 1986;137:525–529; Marti H. P. et al., "Homology cloning of rat 72 kDa type IV collagenase: Cytokine and second-messenger inducibility in mesangial cells," *Biochem. J.*, 1993;291 :441–446; Marti H. P. et al., "Transforming growth factor-b stimulates glomerular mesangial cell synthesis of the 72 kDa type IV collagenase," *Am. J. Pathol.*, 1994;144:82–94). These metalloproteinases are believed to be intimately involved in the aberrant tissue remodeling and cell proliferation characteristic of renal diseases, such as, IgA nephropathy which can progress to through a process of gradual glomerular fibrosis and loss of functional GBM to end-stage renal disease. Metalloproteinase expression has already been well-characterized in experimental immune complex-mediated glomerulonephritis such as the anti-Thy 1.1 rat model (Bagchus W. M., Hoedemaeker P. J., Rozing J., Bakker W. W., "Glomerulonephritis induced by monoclonal anti-Thy 1.1 antibodies: A sequential histological and ultrastructural study in the rat," *Lab. Invest.*, 1986;55:680–687; Lovett D. H., Johnson R. J., Marti H. P., Martin J., Davies M., Couser W. G., "Structural characterization of the mesangial cell type IV collagenase and enhanced expression in a model of immune complex mediated glomerulonephritis," *Am. J. Pathol.*, 1992;141:85–98).

Unfortunately, at present, there are very limited therapeutic strategies for modifying the course of progressive renal disease. Although many renal diseases have an inflammatory component, their responses to standard immunosuppressive regimes are unpredictable and potentially hazardous to individual patients. The secondary consequences of gradual nephron failure such as activation of the reninangiotensin system, accompanied by individual nephron glomerular hyperfiltration and renal hypertension, may be effectively treated with ACE inhibitors or angiotensin II receptor antagonists; but at best, these compounds can only reduce the rate of GFR decline.

A novel strategy to treat at least some renal diseases has been suggested by recent observations of MMP behavior. A rat mesangial cell MMP has been cloned (MMP-2) which is regulated in a tissue specific manner, and in contrast to other cellular sources such as tumor cell lines, is induced by cytokines (Brown P. D., Levy A. T., Margulies I., Liotta L. A., Stetler-Stevenson W. G., "Independent expression and cellular processing of Mr 72,000 type IV collagenase and interstitial collagenase in human tumorigenic cell lines," *Cancer Res.*, 1990;50:6184–6191; Marti H. P. et al., "Homology cloning of rat 72 kDa type IV collagenase: Cytokine and second-messenger inducibility in mesangial cells," *Biochem. J.*, 1993;291:441–446). While MMP-2 can specifically degrade surrounding ECM, it also affects the phenotype of adjacent mesangial cells. Inhibition of MMP-2 by antisense oligonucleotides or transfection techniques can induce a reversion of the proliferative phenotype of cultured mesangial cells to a quiescent or non-proliferative phenotype mimicking the natural in vitro behavior of these cells (Kitamura M. et al., "Gene transfer of metalloproteinase transin induces aberrant behaviour of cultured mesangial cells," *Kidney Int.*, 1994;45:1580–1586; Turck J. et al., "Matrix metalloproteinase 2 (gelatinase A) regulates glomerular mesangial cell proliferation and differentiation," *J. Biol. Chem.*, 1996;271:15074–15083).

Inhibitors of MMP (MMPi) clearly have potential clinical applications in a host of diseases characterized by disturbance of extracellular matrix-cell interactions resulting in abnormal tissue remodeling (Vincenti M. P. et al., "Using inhibitors of metalloproteinases to treat arthritis," *Arthritis Rheum.*, 1994;8:1115–1126; Grams F. et al., "X-ray structures of human neutrophil collagenase complexed with peptide hydroxamate and peptide thiol inhibitors. Implications for substrate binding and rational drug design," *Eur. J. Biochem.*, 1995;228:830–841).

We have identified a series of tricyclic heteroaromatic compounds and their derivatives that are inhibitors of matrix metalloproteinases, particularly collagenase-3, stromelysin-1 and gelatinase A, and thus useful as agents for the treatment of multiple sclerosis, atherosclerotic plaque rupture, restenosis, aortic aneurism, heart failure, left ventricular dilation, periodontal disease, corneal ulceration, treatment of burns, decubital ulcers, wound repair, cancer, inflammation, pain, arthritis, osteoporosis, renal disease, or other autoimmune or inflammatory diseases dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's diseases, prion diseases, myasthenic gravis, and Duchenne's muscular dystrophy.

SUMMARY OF THE INVENTION

Accordingly, a first aspect of the present invention is a compound of Formula I

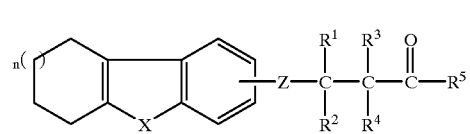

wherein n is zero or an integer of 1 or 2;

X is —O—,

—S(O)$_p$— wherein p is zero or an integer of 1 or 2,

wherein R$^6$ is hydrogen, alkyl, acyl, or benzyl,

—CH$_2$—, or

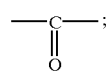

Z is

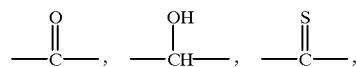

CF$_2$,

CHF,

—CH$_2$—,

wherein R$^7$ is OR$^8$ wherein R$^8$ is hydrogen, alkyl,

—(CH$_2$)$_m$-aryl wherein m is zero or an integer of 1 to 6,

—(CH$_2$)$_m$-heteroaryl wherein m is as defined above,

—(CH$_2$)$_m$-cycloalkyl wherein m is as defined above or

wherein $R^9$ and $R^{9a}$ are either the same or different and are
  hydrogen,
  alkyl,
  aryl,
  arylalkyl,
  heteroaryl, or
  cycloalkyl;
$R^1$, $R^2$, $R^3$, and $R^4$ are either the same or different and are
  hydrogen,
  fluorine,
  alkyl,
  alkenyl,
  alkynyl,
  arylalkenyl,
  heteroarylalkenyl,
  arylapynyl,
  heteroarylalkenyl,
  —$(CH_2)_m$-aryl wherein m is as defined above,
  —$(CH_2)_m$-heteroaryl wherein m is as defined above,
  —$(CH_2)_m$-cycloalkyl wherein m is as defined above,
  —$(CH_2)_q$—$X^a$—$(CH_2)_{q^1}$-alkyl wherein $X^a$ is O, S, SO, $SO_2$, or NH, and q and $q^1$ are each zero or an integer of 1 to 6, and the sum of $q+q^1$ is not greater than six,
  —$(CH_2)_q$—$X^a$—$(CH_2)_{q^1}$-aryl wherein $X^a$, q, and $q^1$ are as defined above,
  —$(CH_2)_q$—$X^a$—$(CH_2)_{q^1}$-heteroa wherein $X_a$, q, and $q^1$ are as defined above, or
  —$(CH_2)_m$—$R^{10}$ wherein $R^{10}$ is

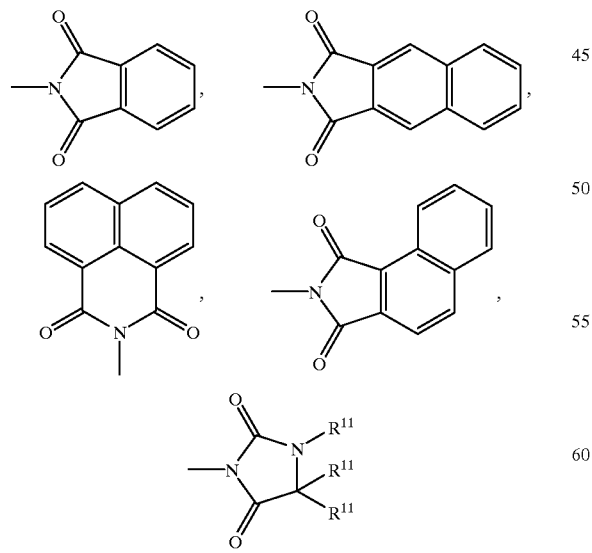

wherein $R^{11}$ is hydrogen, alkyl, aryl, arylalkyl, heteroaryl, or cycloalkyl,

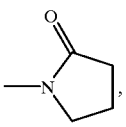 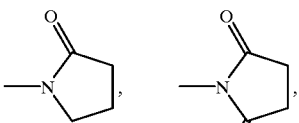

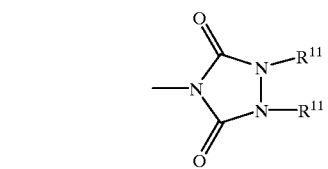

wherein $R_{11}$ is as defined above,

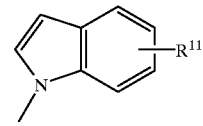

wherein $R_{11}$ is as defined above,

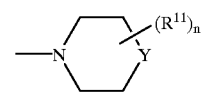

wherein Y is nitrogen, oxygen, sulfur, or $CH_2$ and $R^{11}$ and n are as defined above and m is as defined above, $OR^{11}$ wherein $R^{11}$ is as defined above,

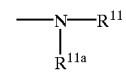

wherein $R^{11}$ and $R^{11a}$ are the same or different and are as defined above for $R^{11}$, —$SR^{11}$ wherein $R^{11}$ is as defined above,

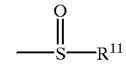

wherein $R^{11}$ is as defined above,

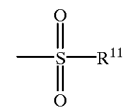

wherein $R^{11}$ is as defined above

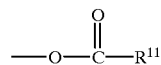

wherein $R^{11}$ is as defined above,

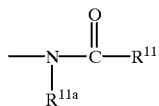

wherein $R^{11}$ and $R^{11a}$ are the same or different and are as defined above for $R^{11}$,

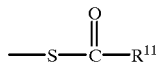

wherein $R^{11}$ is as defined above,

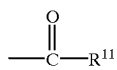

wherein $R^{11}$ is as defined above,

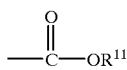

wherein $R^{11}$ is as defined above, or

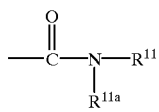

wherein $R^{11}$ and $R^{11a}$ are the same or different and are as defined above for $R^6$, or

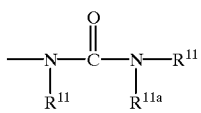

wherein $R^{11}$ and $R^{11a}$ are as defined above; and $R^5$ is
—$OR^{12}$ wherein $R^{12}$ is
hydrogen,
alkyl, or
benzyl,
—NH—$OR^{12}$ wherein $R^{12}$ is as defined above, or
—SH;
with the proviso that when n is 1, X is —O—, Z is

and $R^5$ is $OR^{12}$ wherein $R^{12}$ is as defined above, then at least one of $R^1$, $R^2$, $R^3$, and $R^4$ is not hydrogen; and corresponding isomers thereof; or a pharmaceutically acceptable salt thereof.

As matrix metalloproteinase inhibitors, the compounds of Formula I are useful as agents for the treatment of multiple sclerosis. They are also useful as agents for the treatment of atherosclerotic plaque rupture, aortic aneurism, heart failure, left ventricular dilation, restenosis, periodontal disease, corneal ulceration, treatment of burns, decubital ulcers, wound repair, cancer metastasis, tumor angiogenesis, inflammation, pain, arthritis, osteoporosis, renal disease, and other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

A still further embodiment of the present invention is a pharmaceutical composition for administering an effective amount of a compound of Formula I in unit dosage form in the treatment methods mentioned above. Finally, the present invention is directed to methods for production of compounds of Formula I.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "alkenyl" means a straight or branched unsaturated hydrocarbon radical having from 2 to 10 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, and the like.

The term "alkynyl" means a straight or branched triple bonded unsaturated hydrocarbon radical having from 2 to 10 carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 7 carbon atoms optionally containing an oxygen or sulfur atom and includes, for example, cyclopropyl, cyclobutyl, cyclopentyl, cyclohexyl, cycloheptyl, and the like.

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, guanidino, amidino, $SO_3H$, CHO,

as defined above for alkyl,

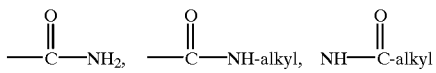

as defined above for alkyl,

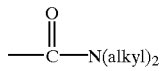

as defined above for alkyl, —(CH$_2$)$_n$2—NH$_2$ wherein n$^2$ is an integer of 1 to 5, —(CH$_2$)$_n$2—NH—alkyl as defined above for alkyl and n$^2$, —(CH$_2$)$_n$2—N(alkyl)$_2$ as defined above for alkyl and n$^2$,

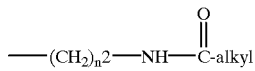

as defined above for alkyl, and n$^2$ and

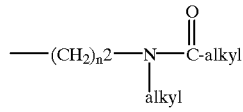

as defined above for alkyl and n$^2$.

The term "arylalkyl" means an aromatic radical attached to an alkyl radical wherein aryl and alkyl are as defined above for example benzyl, phenylethyl, 3-phenylpropyl, (4-chlorophenyl)methyl, and the like.

The term "arylalkenyl" means an aromatic radical attached to an alkenyl radical wherein aryl and alkyl are as defined above.

The term "arylalkynyl" means an aromatic radical attached to an alkynyl radical wherein aryl and alkynyl are as defined above.

The term "heteroaryl" means a 5- and 6-membered heteroaromatic radical containing 1 to 3 heteroatoms selected from N, O, and S and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl 3-, 4-, or 5-isothiazolyl, 2-, 4-, or 5-imidazolyl, 3-, 4-, or 5-pyrazolyl, or 2- or 5-thiadiazolyl optionally substituted by a substituent selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, guanidino, amidino, SO$_3$H, CHO,

as defined above for alkyl,

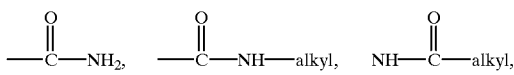

as defined above for alkyl,

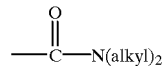

as defined above for alkyl, —(CH$_2$)$_n$2—NH$_2$ wherein n$^2$ is an integer of 1 to 5, —(CH$_2$)$_n$2—NH-alkyl as defined above for alkyl and n$^2$, —(CH$_2$)$_n$2—N(alkyl)$_2$ as defined above for alkyl and n$^2$,

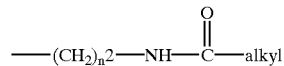

as defined above for alkyl, and n$^2$ and

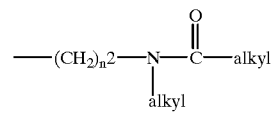

as defined above for alkyl and n$^2$.

The term "heteroarylalkenyl" means a heteroaryl radical attached to an alkenyl radical wherein heteroaryl and alkenyl are as defined above.

The term "heteroarylalkyl" means a heteroaryl radical attached to an alkynyl radical wherein heteroaryl and alkynyl are as defined above.

The term "acyl" means a group of the formula

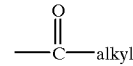

wherein alkyl is as defined above.

"Halogen" is fluorine, chlorine, bromine, or iodine.

"Alkali metal" is a metal in Group IA of the periodic table and includes, for example, lithium, sodium, potassium, and the like.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *J. of Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M. et al., "Pharmaceutical Salts," *J. of Pharma Sci.*, 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

A preferred compound of Formula I is

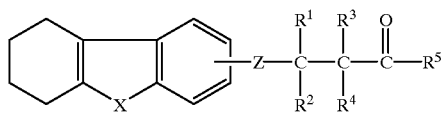

wherein X, Z, $R^1$, $R^2$, $R^3$, $R^4$, and $R^5$ are as defined above.

Another preferred compound of Formula I is

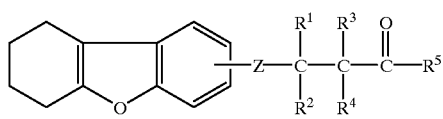

wherein Z, $R^1$, $R^2$, $R^3$, $R^4$, and $R^5$ are as defined above.

Another preferred compound of Formula I is

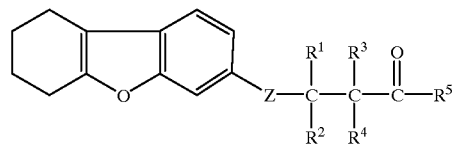

wherein Z, $R^1$, $R^2$, $R^3$, $R^4$, and $R_5$ are as defined above.

Another preferred compound of Formula I is

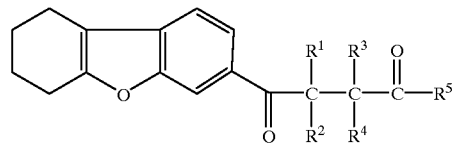

wherein $R^1$, $R^2$, $R^3$, $R^4$, and $R^5$ are as defined above.

A more preferred compound of Formula I is

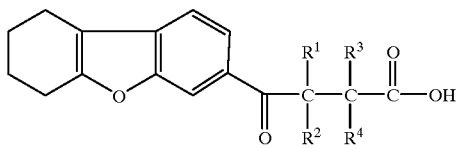

wherein $R^1$, $R^2$, $R^3$, and $R^4$ are as defined above.

A most preferred compound of Formula I is

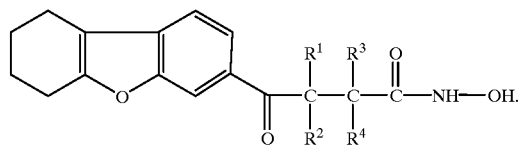

Particularly valuable in this embodiment of the invention is a compound selected from the group consisting of:
- 4-Hydroxyimino-4-(6,7,8,9-tetrahydro-dibenzofuran-3-yl)-butyric acid;
- N-Hydroxy-4-hydroxyimino-4-(6,7,8,9-tetrahydro-dibenzofuran-3-yl)-butyramide;
- N-Hydroxy-4-oxo-4-(6,7,8,9-tetrahydro-dibenzofuran-3-yl)-butyramide;
- 4-(2,3-Dihydro-1-H-8-oxa-cyclopenta[a]inden-6-yl)-4-hydroxyiminobutyric acid;
- 4-(2,3-Dihydro-1H-8-oxa-cyclopenta[a]inden-6-yl)-4-oxo-butyric acid;
- 4-Oxo-2-phenethyl-4-(6,7,8,9-tetrahydro-dibenzofuran-3-yl)-butyric acid;
- 2-[2-Oxo-2-(6,7,8,9-tetrahydro-dibenzofuran-3-yl)-ethyl]-5-phenyl-pentanoic acid;
- 2-[2-Oxo-2-(6,7,8,9-tetrahydro-dibenzofuran-3-yl)-ethyl]-6-phenyl-hexanoic acid;
- 2-[2-Oxo-2-(6,7,8,9-tetrahydro-dibenzofuran-3-yl)-ethyl]-7-phenyl-heptanoic acid;
- 2-[2-Oxo-2-(6,7,8,9-tetrahydro-dibenzofuran-3-yl)-ethyl]-8-phenyl-octanoic acid;
- (S) 4-Hydroxyimino-2-phenethyl4-(6,7,8,9-tetrahydro-dibenzofuran-3-yl)-butyric acid;
- (S) 2-[2-Hydroxyimino-2-(6,7,8,9-tetrahydro-dibenzofuran-3-yl)-ethyl]-5-phenyl-pentanoic acid;

(S) 2-[2-Hydroxyimino-2-(6,7,8,9-tetrahydro-dibenzofuran-3-yl)-ethyl]-6-phenyl-hexanoic acid;

(S) 2-[2-Hydroxyimino-2-(6,7,8,9-tetrahydro-dibenzofuran-3-yl)-ethyl]-7-phenyl-heptanoic acid;

(S) 2-[2-Hydroxyimino-2-(6,7,8,9-tetrahydro-dibenzofuran-3-yl)-ethyl]-8-phenyl-octanoic acid;

(S) 2-(1,3-Dioxo-1,3-dihydro-isoindol-2-ylmethyl)-4-oxo-4-(6,7,8,9-tetrahydro-dibenzofuran-3-yl)-butyric acid;

(S) 2-[2-(1,3-Dioxo-1,3-dihydro-isoindol-2-yl)-ethyl]-4-oxo-4-(6,7,8,9-tetrahydro-dibenzofuran-3-yl)-butyric acid;

(S) 5-(1,3-Dioxo-1,3-dihydro-isoindol-2-yl)-2-[2-oxo-2-(6,7,8,9-tetrahydro-dibenzofuran-3-yl)-ethyl]-pentanoic acid;

(S) 2-(1,3-Dioxo-1,3-dihydro-isoindol-2-ylmethyl)-4-hydroxyimino-4-(6,7,8,9-tetrahydro-dibenzofuran-3-yl)-butyric acid;

(S) 2-[2-(1,3-Dioxo-1,3-dihydro-isoindol-2-yl)-ethyl]-4-hydroxyimino-4-(6,7,8,9-tetrahydro-dibenzofuran-3-yl)-butyric acid;

(S) 5-(1,3-Dioxo-1,3-dihydro-isoindol-2-yl)-2-[2-hydroxyimino-2-(6,7,8,9-tetrahydro-dibenzofuran-3-yl)-ethyl]-pentanoic acid;

(S) 4-Oxo-4-(6,7,8,9-tetrahydro-dibenzofuran-3-yl)-2-(3,4,4-trimethyl-2,5-dioxo-imidazolidin-1-ylmethyl)-butyric acid;

(S) 4-Oxo-4-(6,7,8,9-tetrahydro-dibenzofuran-3-yl)-2-[2-(3,4,4-trimethyl-2,5-dioxo-imidazolidin-1-yl)-ethyl]-butyric acid;

(S) 2-[2-Oxo-2-(6,7,8,9-tetrahydro-dibenzofuran-3-yl)-ethyl]-5-(3,4,4-trimethyl-2,5-dioxo-imidazolidin-1-yl)-pentanoic acid;

(S) 4-Hydroxyimino-4-(6,7,8,9-tetrahydro-dibenzofuran-3-yl)-2-(3,4,4-trimethyl-2,5-dioxo-imidazolidin-1-ylmethyl)-butyric acid;

(S) 4-Hydroxyimino-4-(6,7,8,9-tetrahydro-dibenzofuran-3-yl)-2-[2-(3,4,4-trimethyl-2,5-dioxo-imidazolidin-1-yl)-ethyl]-butyric acid;

(S) 2-[2-Hydroxyimino-2-(6,7,8,9-tetrahydro-dibenzofuran-3-yl)-ethyl]-5-(3,4,4-trimethyl-2,5-dioxo-imidazolidin-1-yl)-pentanoic acid;

(S) 4-(2,3-Dihydro-1H-8-oxa-cyclopenta[a]inden-6-yl)-4-oxo-2-phenethyl-butyric acid; (S) 2-[2-(2,3-Dihydro-1H-8-oxa-cyclopenta[a]inden-6-yl)-2-oxo-ethyl]-6-phenyl-hexanoic acid;

(S) 2-[2-(2,3-Dihydro-1H-8-oxa-cyclopenta[a]inden-6-yl)-2-oxo-ethyl]-7-phenyl-heptanoic acid;

(S) 2-[2-(2,3-Dihydro-1H-8-oxa-cyclopenta[a]inden-6-yl)-2-oxo-ethyl]-5-phenyl-pentanoic acid;

(S) 2-[2-(2,3-Dihydro-1H-8-oxa-cyclopenta[a]inden-6-yl)-2-oxo-ethyl]-8-phenyl-octanoic acid;

(S) 2-[2-(2,3-Dihydro-1H-8-oxa-cyclopenta[a]inden-6-yl)-2-hydroxyimino-ethyl]-8-phenyl-octanoic acid;

(S) 2-[2-(2,3-Dihydro-1H-8-oxa-cyclopenta[a]inden-6-yl)-2-hydroxyimino-ethyl]-7-phenyl-heptanoic acid;

(S) 2-[2-(2,3-Dihydro-1H-8-oxa-cyclopenta[a]inden-6-yl)-2-hydroxyimino-ethyl]-6-phenyl-hexanoic acid;

(S) 2-[2-(2,3-Dihydro-1H-8-oxa-cyclopenta[a]inden-6-yl)-2-hydroxyimino-ethyl]-5-phenyl-pentanoic acid;

(S) 4-(2,3-Dihydro-1H-8-oxa-cyclopenta[a]inden-6-yl)4-hydroxyimino-2-phenethyl-butyric acid;

(S) 4-(2,3-Dihydro-1H-8-oxa-cyclopenta[a]inden-6-yl)-2-[2-(1,3-dioxo-1,3-dihydro-isoindol-2-yl)-ethyl]-4-oxo-butyric acid;

(S) 2-[2-(2,3-Dihydro-1H-8-oxa-cyclopenta[a]inden-6-yl]-2-oxo-ethyl]-5-(1,3-dioxo-1,3-dihydro-isoindol-2-yl)-pentanoic acid;

(S) 2-[2-(2,3-Dihydro-1H-8-oxa-cyclopenta[a]inden-6-yl)-2-oxo-ethyl]-6-(1,3-dioxo-1,3-dihydro-isoindol-2-yl)-hexanoic acid;

(S) 2-[2-(2,3-Dihydro-1H-8-oxa-cyclopenta[a]inden-6-yl)-2-oxo-ethyl]-7-(1,3-dioxo-1,3-dihydro-isoindol-2-yl)-heptanoic acid;

(S) 2-[2-(2,3-Dihydro-1H-8-oxa-cyclopenta[a]inden-6-yl)-2-oxo-ethyl]-8-(1,3-dioxo-1,3-dihydro-isoindol-2-yl)-octanoic acid;

(S) 4-(2,3-Dihydro-1H-8-oxa-cyclopenta[a]inden-6-yl)-2-[2-(1,3-dioxo-1,3-dihydro-isoindol-2-yl)-ethyl]-4-hydroxyimino-butyric acid;

(S) 2-[2-(2,3-Dihydro-1H-8-oxa-cyclopenta[a]inden-6-yl)-2-hydroxyimino-ethyl]-5-(1,3-dioxo-1,3-dihydro-isoindol-2-yl)-pentanoic acid;

(S) 2-[2-(2,3-Dihydro-1H-8-oxa-cyclopenta[a]inden-6-yl)-2-hydroxyimino-ethyl]-6-(1,3-dioxo 1,3-dihydro-isoindol-2-yl)-hexanoic acid;

(S) 2-[2-(2,3-Dihydro-1H-8-oxa-cyclopenta[a]inden-6-yl)-2-hydroxyimino-ethyl]-7-(1,3-dioxo-1,3-dihydro-isoindol-2-yl)-heptanoic acid;

(S) 2-[2-(2,3-Dihydro-1H-8-oxa-cyclopenta[a]inden-6-yl)-2-hydroxyimino-ethyl]-8-(1,3dioxo-1,3-dihydro-isoindol-2-yl)-octanoic acid;

(S) 4(2,3-Dihydro-1H-8-oxa-cyclopenta[a]inden-6-yl)-2-(4,4-dimethyl-2,5-dioxo-imidazolidin-1-ylmethyl)4-oxo-butyric acid;

(S) 4-(2,3-Dihydro-1H-8-oxa-cyclopenta[a]inden-6-yl)-2-(1H-indol-3-ylmethyl)-4-oxo-butyric acid;

(S) 4-(2,3-Dihydro-1H-8-oxa-cyclopenta[a]inden-6-yl)-2-[2-(4,4-dimethyl-2,5-dioxo-imidazolidin-1-yl)-ethyl]-4-oxo-butyric acid;

(S) 2-[2-(2,3-Dihydro-1H-8-oxa-cyclopenta[a]inden-6-yl)-2-oxo-ethyl]-5-(4,4-dimethyl-2,5-dioxo-imidazolidin-1-yl)-pentanoic acid;

(S) 4-(2,3-Dihydro-1H-8-oxa-cyclopenta[a]inden-6yl)-2-[2-(4,4-dimethyl-2,5-dioxo-imidazolidin-1-yl)-ethyl]--4--hydroxyimino-butyric acid;

(S) 4-(2,3-Dihydro-1H-8-oxa-cyclopenta[a]inden-6-yl)-2-(4,4-dimethyl-2,5-dioxo-imidazolidin-1-ylmethyl)-4-hydroxyimino-butyric acid;

(S) 4-(2,3-Dihydro-1H-8-oxa-cyclopenta[a]inden-6-yl)-2-[2-(4,4-dimethyl-2,5-dioxo-imidazolidin-1-yl)-ethyl]-4--hydroxyimino-butyric acid;

(S) 4-(2,3-Dihydro-1H-8-oxa-cyclopenta[a]inden-6-yl)-2-[2-(1H-indol-3-yl)-ethyl]-4-oxo-butyric acid;

(S) 2-[2-(2,3-Dihydro-1H-8-oxa-cyclopenta[a]inden-6-yl)-2-oxo-ethyl]-5-(1H-indol-3yl)pentanoic acid;

(S) 2-[2-(2,3-Dihydro-1H-8-oxa-cyclopenta[a]inden-6-yl)-2-oxo-ethyl]-6-(1H-indol-3-yl)-hexanoic acid;

(S) 2-[2-(2,3-Dihydro-1H-8-oxa-cyclopenta[a]inden-6-yl)-2-hydroxyimino-ethyl]-5-(1H-indol-3-yl)-pentanoic acid;

(S) 2-[2-(2,3-Dihydro-1H-8-oxa-cyclopenta[a]inden-6-yl)-2-hydroxyimino-ethyl]-6-(1H-indol-3-yl)-hexanoic acid;

(S) 2-[2-(2,3-Dihydro-1H-8-oxa-cyclopenta[a]inden-6-yl)-2-oxo-ethyl]-7-(1H-indol-3-yl)heptanoic acid;

(S) 2-[2-(2,3-Dihydro-1H-8-oxa-cyclopenta[a]inden-6-yl)-2-oxo-ethyl]-8-(1H-indol-3-yl)-octanoic acid;

(S) 4-(2,3-Dihydro-1H-8-oxa-cyclopenta[a]inden-6-yl)-4-hydroxyimino-2-(1H-indol-3-ylmethyl)-butyric acid;

(S) 4-(2,3-Dihydro-1H-8-oxa-cyclopenta[a]inden-6-yl)-4-hydroxyimino-2-[2-(1H-indol-3-yl)-ethyl]-butyric acid;

(S) 2-[2-(2,3-Dihydro-1H-8-oxa-cyclopenta[a]inden-6-yl)-2-hydroxyimino-ethyl]-8-(1H-indol-3-yl)-octanoic acid;

(S) 2-[2-(2,3-Dihydro-1H-8-oxa-cyclopenta[a]inden-6-yl)-2-hydroxyimino-ethyl]-7-(1H-indol-3-yl)-heptanoic acid;

4-(2,3-Dihydro-1H-8-oxa-cyclopenta[a]inden-6yl)-4-hydroxy-butyric acid;

4-Hydroxy-2-phenethyl-4-(6,7,8,9-tetrahydro-dibenzofuran-3-yl)-butyric acid;

2-[2-Hydroxy-2-(6,7,8,9-tetrahydro-dibenzofuran-3-yl)-ethyl]-5-phenyl-pentanoic acid;

2-[2-Hydroxy-2-(6,7,8,9-tetrahydro-dibenzofuran-3-yl)-ethyl]-6-phenyl-hexanoic acid;

2-[2-Hydroxy-2-(6,7,8,9-tetrahydro-dibenzofuran-3-yl)-ethyl]-7-phenyl-heptanoic acid;

2-[2-Hydroxy-2-(6,7,8,9-tetrahydro-dibenzofuran-3-yl)-ethyl]-8-phenyl-octanoic acid;

4-Hydroxy-4-(6,7,8,9-tetrahydro-dibenzofuran-3-yl)-2-(3,4,4-trimethyl-2,5-dioxo-imidazolidin-1-ylmethyl)-butyric acid;

4-Hydroxy4-(6,7,8,9-tetrahydro-dibenzofuran-3-yl)-2-[2-(3,4,4-trimethyl-2,5-dioxo-imidazolidin-1-yl)-ethyl]-butyric acid;

2-[2-Hydroxy-2-(6,7,8,9-tetrahydro-dibenzofuran-3-yl)-ethyl-5-(3,4,4-trimethyl-2,5-dioxo-imidazolidin-1-yl)-pentanoic acid;

4(2,3-Dihydro-1H-8-oxa-cyclopenta[a]inden-6-yl)-4-hydroxy-butyric acid;

4-Oxo-4--(6,7,8,9-tetrahydro-5H-fluoren-2-yl)-butyric acid;

(S) 4-Oxo-2-phenethyl-4--(6,7,8,9-tetrahydro-5H-fluoren-2-yl)-butyric acid;

(S) 2-[2-Oxo-2-(6,7,8,9-tetrahydro-5H-fluoren-2-yl)-ethyl]-5-phenyl-pentanoic acid;

(S) 2-[2-Oxo-2-(6,7,8,9-tetrahydro-5H-fluoren-2-yl)-ethyl]-6-phenyl-hexanoic acid;

(S) 2-[2-Oxo-2-(6,7,8,9-tetrahydro-5H-fluoren-2-yl)-ethyl]-7-phenyl-heptanoic acid;

(S) 2-[2-Oxo-2-(6,7,8,9-tetrahydro-5H-fluoren-2-yl)-ethyl]-8-phenyl-octanoic acid;

4-Hydroxyimino-4-(6,7,8,9-tetrahydro-5H-fluoren-2-yl)-butyric acid;

(S) 4-Hydroxyimino-2-phenethyl]-4--(6,7,8,9-tetrahydro-5H-fluoren-2-yl)-butyric acid;

(S) 2-[2-Hydroxyimino-2-(6,7,8,9-tetrahydro-5H-fluoren-2-yl)-ethyl]-5-phenyl-pentanoic acid;

(S) 2-[2-Hydroxyimino-2-(6,7,8,9-tetrahydro-5H-fluoren-2-yl)-ethyl]-6-phenyl-hexanoic acid;

(S) 2-[2-Hydroxyimino-2-(6,7,8,9-tetrahydro-5H-fluoren-2-yl)-ethyl]-7-phenyl-heptanoic acid;

(S) 2-[2-Hydroxyimino-2-(6,7,8,9-tetrahydro-5H-fluoren-2-yl)-ethyl]-8-phenyl-octanoic acid;

(S) 4-Oxo-4-(6,7,8,9-tetrahydro-5H-fluoren-2-yl)-2-(3,4,4-trimethyl-2,5-dioxo-imidazolidin-1-ylmethyl)-butyric acid;

(S) 4-Oxo-4-(6,7,8,9-tetrahydro-5H-fluoren-2-yl)-2-[2-(3,4,4-trimethyl-2,5-dioxo-imidazolidin-1-yl)-ethyl]-butyric acid;

(S) 2-[2-Oxo-2-(6,7,8,9-tetrahydro-5H-fluoren-2-yl)-ethyl]-5-(3,4,4-trimethyl-2,5-oxo-imidazolidin-1-yl)-pentanoic acid;

(S) 4-Hydroxyimino-4-(6,7,8,9-tetrahydro-5H-fluoren-2-yl)-2-(3,4,4-trimethyl-2,5-dioxo-imidazolidin-1-ylmethyl)-butyric acid;

(S) 4-Hydroxyimino-4-(6,7,8,9-tetrahydro-5H-fluoren-2-yl)2-[2-(3,4,4-trimethyl-2,5-dioxo-imidazolidin-1-yl)-ethyl]-butyric acid;

(S) 2-[2-Hydroxyimino-2-(6,7,8,9-tetrahydro-5H-fluoren-2-yl)-ethyl]-5-(3,4,4-trimethyl-2,5-dioxo-imidazolidin-1-yl)-pentanoic acid;

(S) 2-(1,3-Dioxo-1,3-dihydro-isoindol-2-ylmethyl)-4-oxo-4-(6,7,8,9-tetrahydro-5H-fluoren-2-yl)-butyric acid;

(S) 2-[2-(1,3-Dioxo-1,3-dihydro-isoindol-2-yl)-ethyl]-4-oxo-4-(6,7,8,9-tetrahydro-5H-fluoren-2-yl)-butyric acid;

(S) 5-(1,3-Dioxo-1,3-dihydro-isoindol-2-yl)-2-[2-oxo-2-(6,7,8,9-tetrahydro-5H-fluoren-2-yl)-ethyl]-pentanoic acid;

(S) 2-(1,3-Dioxo-1,3-dihydro-isoindol-2-ylmethyl)-4-hydroxyimino-4-(6,7,8,9-tetrahydro-5H-fluoren-2-yl)-butyric acid;

(S) 2-[2-(1,3-Dioxo-1,3-dihydro-isoindol-2-yl)-ethyl]-4-hydroxyimino-4-(6,7,8,9-tetrahydro-5H-fluoren-2-yl)-butyric acid;

(S) 5-(1,3-Dioxo-1,3-dihydro-isoindol-2-yl)-2-[2-hydroxyimino-2-(6,7,8,9-tetrahydro-5H-fluoren-2-yl)-ethyl]-pentanoic acid;

4-(9-Methyl-6,7,8,9-tetrahydro-5H-carbazol-2-yl)-4-oxo-butyric acid;

4-Hydroxyimino-4--(9-methyl-6,7,8,9-tetrahydro-5H-carbazol-2-yl)-butyric acid;

4-Oxo-4--(6,7,8,9-tetrahydro-5H-10-oxa-benzo[a]azulen-2-yl)-butyric acid;

4-Hydroxyimino-4-(6,7,8,9-tetrahydro-5H-10-oxa-benzo[a]azulen-2-yl)-butyric acid;

(S) 4-Oxo-2-phenethyl-4-(6,7,8,9-tetrahydro-5H-10-oxa-benzo[a]azulen-2-yl)-butyric acid;

(S) 2-[2-Oxo-2-(6,7,8,9-tetrahydro-5H-10-oxa-benzo[a]azulen-2-yl)-ethyl]-5-phenyl-pentanoic acid;

(S) 2-[2-Oxo-2-(6,7,8,9-tetrahydro-5H-10-oxa-benzo[a]azulen-2-yl)-ethyl]-6-phenyl-hexanoic acid;

(S) 2-[2-Oxo-2-(6,7,8,9-tetrahydro-5H-10-oxa-benzo[a]azulen-2-yl)-ethyl]-7-phenyl-heptanoic acid;

(S) 2-[2-Oxo-2-(6,7,8,9-tetrahydro-5H-10-oxa-benzo[a]azulen-2-yl)-ethyl]-8-phenyl-octanoic acid;

(S) 4-Hydroxyimino-2-phenethyl-4-(6,7,8,9-tetrahydro-5H-10-oxa-benzo[a]azulen-2-yl)-butyric acid;

(S) 2-[2-Hydroxyimino-2-(6,7,8,9-tetrahydro-5H-10-oxa-benzo[a]azulen-2-yl)-ethyl]-5-phenyl-pentanoic acid;

(S) 2-[2-Hydroxyimino-2-(6,7,8,9-tetrahydro-5H-10-oxa-benzo[a]azulen-2-yl)-ethyl]-6-phenyl-hexanoic acid;

(S) 2-[2-Hydroxyimino-2-(6,7,8,9-tetrahydro-5H-10-oxa-benzo[a]azulen-2-yl)-ethyl]-7-phenyl-heptanoic acid;

(S) 2-[2-Hydroxyimino-2-(6,7,8,9-tetrahydro-5H-10-oxa-benzo[a]azulen-2-yl)-ethyl]-8-phenyl-octanoic acid;

4-Oxo--4-(6,7,8,9-tetrahydro-dibenzothiophen-3-yl)-butyric acid;

4-Hydroxyimino--4-(6,7,8,9-tetrahydro-dibenzothiophen-3-yl)-butyric acid;

(S) 4-Oxo-4-(6,7,8,9-tetrahydro-dibenzothiophen-3-yl)-2-(3,4,4-trimethyl-2,5-dioxo-imidazolidin-1-ylmethyl)-butyric acid;

(S) 4-Oxo-4-(6,7,8,9-tetrahydro-dibenzothiophen-3-yl)-2-[2-(3,4,4-trimethyl-2,5-dioxo-imidazolidin-1-yl)-ethyl]-butyric acid;

(S) 2-[2-Oxo-2-(6,7,8,9-tetrahydro-dibenzothiophen-3-yl)-ethyl]-5-(3,4,4-trimethyl-2,5-dioxo-imidazolidin-1-yl)-pentanoic acid;

(S) 4-Hydroxyimino-4-(9-methyl-6,7,8,9-tetrahydro-5H-carbazol-2-yl)-2-phenethyl-butyric acid;

(S) 2-[Hydroxyimino-2-(9-methyl-6,7,8,9-tetrahydro-5H-carbazol-2-yl)-ethyl]-5-phenyl-pentanoic acid;

(S) 2-[2-Hydroxyimino-2-(9-methyl-6,7,8,9-tetrahydro-5H-carbazol-2-yl)-ethyl]-6-phenyl-hexanoic acid;

(S) 2-[2-Hydroxyimino-2-(9-methyl-6,7,8,9-tetrahydro-5H-carbazol-2-yl)-ethyl]-7-phenyl-heptanoic acid;

(S) 2-[2-Hydroxyimino-2-(9-methyl-6,7,8,9-tetrahydro-5H-carbazol-2-yl)-ethyl]-8-phenyl-octanoic acid;

(S) 4-Hydroxyimino-4-(6,7,8,9-tetrahydro-dibenzothiophen-3-yl)-2-(3,4,4-trimethyl-2,5-dioxo-imidazolidin-1-ylmethyl)-butyric acid;

(S) 4-Hydroxyimino-4-(6,7,8,9-tetrahydro-dibenzothiophen-3-yl)-2-[2-(3,4,4-trimethyl-2,5-dioxo-imidazolidin-1-yl)-ethyl]-butyric acid;

(S) 2-[2-Hydroxyimino-2-(6,7,8,9-tetrahydro-dibenzothiophen-3-yl)-ethyl]-5-(3,4,4-trimethyl-2,5-dioxo-imidazolidin-1-yl)-pentanoic acid;

(S) 4(9-Methyl-6,7,8,9-tetrahydro-5H-carbazol-2-yl)-4-oxo-2-phenethyl-butyric acid;

(S) 2-[2-(9-Methyl-6,7,8,9-tetrahydro-5H-carbazol-2-yl)-2-oxo-ethyl]-5-phenyl-pentanoic acid;

(S) 2-[2-(9-Methyl-6,7,8,9-tetrahydro-5H-carbazol-2-yl)-2-oxo-ethyl]-6-phenyl-hexanoic acid;

(S) 2-[2-(9-Methyl-6,7,8,9-tetrahydro-5H-carbazol-2-yl)-2-oxo-ethyl]-7-phenyl-heptanoic acid;

(S) 2-[2-(9-Methyl-6,7,8,9-tetrahydro-5H-carbazol-2-yl)-2-oxo-ethyl]-8-phenyl-octanoic acid;

(R) 4-Hydroxyimino-2-phenethyl-4--(6,7,8,9-tetrahydro-dibenzofuran-3-yl)-butyric acid;

(R) 2-[2-Hydroxyimino-2-(6,7,8,9-tetrahydro-dibenzofuran-3-yl)-ethyl]-5-phenyl-pentanoic acid;

(R) 2-[2-Hydroxyimino-2-(6,7,8,9-tetrahydro-dibenzofuran-3-yl)-ethyl]-6-phenyl-hexanoic acid;

(R) 2-[2-Hydroxyimino-2-(6,7,8,9-tetrahydro-dibenzofuran-3-yl)-ethyl]-7-phenyl-heptanoic acid;

(R) 2-[2-Hydroxyimino-2-(6,7,8,9-tetrahydro-dibenzofuran-3-yl)-ethyl]-8-phenyl-octanoic acid;

(R) 2[-(1,3-Dioxo-1,3-dihydro-isoindol-2-ylmethyl)-4-oxo-4-(6,7,8,9-tetrahydro-dibenzofuran-3-yl)-butyric acid;

(R) 2-[2-(1,3-Dioxo-1,3-dihydro-isoindol-2-yl)-ethyl]-4-oxo-4-(6,7,8,9-tetrahydro-dibenzofuran-3-yl)-butyric acid;

(R) 5-(1,3-Dioxo-1,3-dihydro-isoindol-2-yl)-2-[2-oxo-2-(6,7,8,9-tetrahydro-dibenzofuran-3-yl)-ethyl]-pentanoic acid;

(R) 2-(1,3-Dioxo-1,3-dihydro-isoindol-2-ylmethyl)-4-hydroxyimino-4-(6,7,8,9-tetrahydro-dibenzofuran-3-yl)-butyric acid;

(R) 2-[2-(1,3-Dioxo-1,3-dihydro-isoindol-2-yl)-ethyl]-4-hydroxyimino-4-(6,7,8,9-tetrahydro-dibenzofuran-3-yl)-butyric acid;

(R) 5-(1,3-Dioxo-1,3-dihydro-isoindol-2-yl)-2-[2-hydroxyimino-2-(6,7,8,9-tetrahydro-dibenzofuran-3-yl)-ethyl]-pentanoic acid;

(R) 4-Oxo-4-(6,7,8,9-tetrahydro-dibenzofuran-3-yl)-2-(3,4,4-trimethyl-2,5-dioxo-imidazolidin-1-ylmethyl)-butyric acid;

(R) 4-Oxo-4-(6,7,8,9-tetrahydro-dibenzofuran-3-yl)-2-[2-(3,4,4-trimethyl-2,5-dioxo-imidazolidin-1-yl)-ethyl]-butyric acid;

(R) 2-[2-Oxo-2-(6,7,8,9-tetrahydro-dibenzofuran-3-yl)-ethyl]-5-(3,4,4-trimethyl-2,5-dioxo-imidazolidin-1-yl)-pentanoic acid;

(R) 4-Hydroxyimino-4-(6,7,8,9tetrahydro-dibenzofuran-3-yl)-2-(3,4,4-trimethyl-2,5-dioxo-imidazolidin-1-ylmethyl)-butyric acid;

(R) 4-Hydroxyimino-4-(6,7,8,9-tetrahydro-dibenzofuran-3-yl)-2-[2-(3,4,4-trimethyl-2,5-dioxo-imidazolidin-1-yl)-ethyl]-butyric acid;

(R) 2-[2-Hydroxyimino-2-(6,7,8,9-tetrahydro-dibenzofuran-3-yl)-ethyl]-5-(3,4,4trimethyl-2,5-dioxo-imidazolidin-1-yl)-pentanoic acid;

(R) 4-(2,3-Dihydro-1H-8-oxa-cyclopenta[a]inden-6-yl)-4-oxo-2-phenethyl-butyric acid;

(R) 2-[2-(2,3-Dihydro-1H-8-oxa-cyclopenta[a]inden-6-yl)-2-oxo-ethyl]-6-phenyl-hexanoic acid;

(R) 2-[2-(2,3-Dihydro-1H-8-oxa-cyclopenta[a]inden-6-yl)-2-oxo-ethyl]-7-phenyl-heptanoic acid;

(R) 2-[2-(2,3-Dihydro-1H-8-oxa-cyclopenta[a]inden-6-yl)-2-oxo-ethyl]-5-phenyl-pentanoic acid;

(R) 2-[2-(2,3-Dihydro-1H-8-oxa-cyclopenta[a]inden-6-yl)-2-oxo-ethyl]-8-phenyl-octanoic acid;

(R) 2-[2-(2,3-Dihydro-1H-8-oxa-cyclopenta[a]inden-6-yl)-2-hydroxyimino-ethyl]-8-phenyl-octanoic acid;

(R) 2-[2-(2,3-Dihydro-1H-8-oxa-cyclopenta[a]inden-6-yl)-2-hydroxyimino-ethyl]-7-phenyl-heptanoic acid;

(R) 2-[2-(2,3-Dihydro-1H-8-oxa-cyclopenta[a]inden-6-yl-2-hydroxyimino-ethyl]-6-phenyl-hexanoic acid;

(R) 2-[2-(2,3-Dihydro-1H-8-oxa-cyclopenta[a]inden-6-yl)-2-hydroxyimino-ethyl]-5-phenyl-pentanoic acid;

(R) 4-(2,3-Dihydro-1H-8-oxa-cyclopenta[a]inden-6-yl)-4-hydroxyimino-2-phenethyl-butyric acid;

(R) 4-(2,3-Dihydro-1H-8-oxa-cyclopenta[a]inden-6-yl)-2-[2-(1,3-dioxo-1,3-dihydro-isoindol-2-yl)-ethyl]-4-oxo-butyric acid;

(R) 2-[2-(2,3-Dihydro-1H-8-oxa-cyclopenta[a]inden-6-yl)-2-oxo-ethyl]-5-(1,3-dioxo-1,3-dihydro-isoindol-2-yl)-pentanoic acid;

(R) 2-[2-(2,3-Dihydro-1H-8-oxa-cyclopenta[a]inden-6-yl)-2-oxo-ethyl]-6-(1,3-dioxo-1,3-dihydro-isoindol-2-yl)-hexanoic acid;

(R) 2-[2-(2,3-Dihydro-1H-8-oxa-cyclopenta[a]inden-6-yl)-2-oxo-ethyl]-7-(1,3-dioxo-1,3-dihydro-isoindol-2-yl)-heptanoic acid;

(R) 2-[2-(2,3-Dihydro-1H-8-oxa-cyclopenta[a]inden-6-yl)-2-oxo-ethyl]-8-(1,3-dioxo-1,3-dihydro-isoindol-2-yl)-octanoic acid;

(R) 4-(2,3-Dihydro-1H-8-oxa-cyclopenta[a]inden-6-yl)-2-[2-(1,3-dioxo-1,3-dihydro-isoindol-2-yl-1ethyl]-4-hydroxyimino-butyric acid;

(R) 2-[2-(2,3-Dihydro-1H-8-oxa-cyclopenta[a]inden-6-yl)-2-hydroxyimino-ethyl]-5-(1,3-dioxo-1,3-dihydro-isoindol-2-yl)-pentanoic acid;

(R) 2-[2-(2,3-Dihydro-1H-8-oxa-cyclopenta[a]inden-6-yl)-2-Hydroxyimino-ethyl]-6-(1,3-dioxo-1,3-dihydro-isoindol-2-yl)-hexanoic acid;

(R) 2-[2-(2,3-Dihydro-1H-8-oxa-cyclopenta[a]inden-6-yl)-2-hydroxyimino-ethyl]-7-(1,3-dioxo-1,3-dihydro-isoindol-2-yl)-heptanoic acid;

(R) 2-[2-(2,3-Dihydro-1H-8-oxa-cyclopenta[a]inden-6-yl)-2-hydroxyimino-ethyl]-8-(1,3-dioxo-1,3-dihydro-isoindol-2-yl)-octanoic acid;

(R) 4-(2,3-Dihydro-1H-8-oxa-cyclopenta[a]inden-6-yl)-2-(4,4-dimethyl-2,5-dioxo-imidazolidin-1-ylmethyl)-4-oxo-butyric acid;

(R) 4-(2,3-Dihydro-1H-8-oxa-cyclopenta[a]inden-6-yl)-2-(1H-indol-3-ylmethyl)-4-oxo-butyric acid;

(R) 4-(2,3-Dihydro-1H-8-oxa-cyclopenta[a]inden-6-yl)-2-[2-(4,4-dimethyl-2,5-dioxo-imidazolidin-1-yl)-ethyl]-4-oxo-butyric acid;

(R) 2-[2-(2,3-Dihydro-1H-8-oxa-cyclopenta[a]inden-6-yl)-2-oxo-ethyl]-5-(4,4-dimethyl-2,5-dioxo-imidazolidin-1-yl)-pentanoic acid;

(R) 4(2,3-Dihydro-1H-8-oxa-cyclopenta[a]inden-6-yl)-2-[2-(4,4dimethyl-2,5-dioxo-imidazolidin-1-yl)-ethyl]-4-hydroxyimino-butyric acid;

(R) 4-(2,3-Dihydro-1H-8-oxa-cyclopenta[a]inden-6-yl)-2-(4,4-dimethyl-2,5-dioxo-imidazolidin-1-ylmethyl)-4-hydroxyimino-butyric acid;

R) 4-(2,3-Dihydro-1H-8-oxa-cyclopenta[a]inden-6-yl)-2-[2-(4,4-dimethyl-2,5-dioxo-imidazolidin-1-yl)-ethyl]-4-hydroxyimino-butyric acid;

(R) 4-(2,3-Dihydro-1H-8-oxa-cyclopenta[a]inden-6-yl)-2-[2-(1H-indol-3-yl)-ethyl]-4-oxo-butyric acid;

(R) 2-[2-(2,3-Dihydro-1H-8-oxa-cyclopenta[a]inden-6-yl)-2-oxo-ethyl]-5-(1H-indol-3-yl)-pentanoic acid;

(R) 2-[2-(2,3-Dihydro-1H-8-oxa-cyclopenta[a]inden-6-yl)-2-oxo-ethyl]-6-(1H-indol-3-yl)-hexanoic acid;

(R) 2-[2-(2,3-Dihydro-1H-8-oxa-cyclopenta[a]inden-6-yl)-2-hydroxyimino-ethyl]-5-(1H-indol-3-yl)-pentanoic acid;

(R) 2-[2-(2,3-Dihydro-1H-8-oxa-cyclopenta[a]inden-6-yl)-2-hydroxyimino-ethyl]-6-(1H-indol-3-yl)-hexanoic acid;

(R) 2-[2-(2,3-Dihydro-1H-8-oxa-cyclopenta[a]inden-6-yl)-2-oxo-ethyl]-7-(1H-indol-3-yl)-heptanoic acid;

(R) 2-[2-(2,3-Dihydro-1H-8-oxa-cyclopenta[a]inden-6-yl)-2-oxo-ethyl]-8-(1H-indol-3-yl)-octanoic acid;

(R) 4-(2,3-Dihydro-1H-8-oxa-cyclopenta[a]inden-6-yl)-4-hydroxyimino-2-(1H-indol-3-ylmethyl)-butyric acid;

(R) 4-(2,3-Dihydro-1H-8-oxa-cyclopenta[a]inden-6-yl)-4-hydroxyimino-2-[2-(1H-indol-3-yl)-ethyl]-butyric acid;

(R) 2-[2-(2,3-Dihydro-1H-8-oxa-cyclopenta[a]inden-6-yl)-2-hydroxyimino-ethyl]-8-(1H-indol-3-yl)-octanoic acid;

(R) 2-[2-(2,3-Dihydro-1H-8-oxa-cyclopenta[a]inden-6-yl)-2-hydroxyimino-ethyl]-7-(1H-indol-3-yl)-heptanoic acid;

(R) 4-Oxo-2-phenethyl]-4-(6,7,8,9-tetrahydro-5H-fluoren-2-yl)-butyric acid;

(R) 2-[2-Oxo-2-(6,7,8,9-tetrahydro-5H-fluoren-2-yl)-ethyl]-5-phenyl-pentanoic acid;

(R) 2-[2-Oxo-2-(6,7,8,9-tetrahydro-5H-fluoren-2-yl)-ethyl]-6-phenyl-hexanoic acid;

(R) 2-[2-Oxo-2-(6,7,8,9-tetrahydro-5H-fluoren-2-yl)-ethyl]-7-phenyl-heptanoic acid;

(R) 2-[2-Oxo-2-(6,7,8,9-tetrahydro-5H-fluoren-2-yl)-ethyl]-8-phenyl-octanoic acid;

(R) 4-Hydroxyimino-2-phenethyl-4-(6,7,8,9-tetrahydro-5H-fluoren-2-yl)-butyric acid;

(R) 2-[2-Hydroxyimino-2-(6,7,8,9-tetrahydro-5H-fluoren-2-yl)-ethyl]-5-phenyl-pentanoic acid;

(R) 2-[2-Hydroxyimino-2-(6,7,8,9-tetrahydro-5H-fluoren-2-yl)-ethyl]-6-phenyl-hexanoic acid;

(R) 2-[2-Hydroxyimino-2-(6,7,8,9-tetrahydro-5H-fluoren-2-yl)-ethyl]-7-phenyl-heptanoic acid;

(R) 2-[2-Hydroxyimino-2-(6,7,8,9-tetrahydro-5H-fluoren-2-yl)-ethyl]-8-phenyl-octanoic acid;

(R) 4-Oxo-4-(6,7,8,9-tetrahydro-5H-fluoren-2-yl)-2-(3,4,4-trimethyl-2,5-dioxo-imidazolidin-1-ylmethyl)-butyric acid;

(R) 4-Oxo-4-(6,7,8,9-tetrahydro-5H-fluoren-2-yl)-2-[2-(3,4,4-trimethyl-2,5-dioxo-imidazolidin-1-yl)-ethyl]-butyric acid;

(R) 2-[2-Oxo-2-(6,7,8,9-tetrahydro-5H-fluoren-2-yl)-ethyl]-5-(3,4,4-trimethyl-2,5-dioxo-imidazolidin-1-yl)-pentanoic acid;

(R) 4-Hydroxyimino-4-(6,7,8,9-tetrahydro-5H-fluoren-2-yl)-2-(3,4,4-trimethyl-2,5-dioxo-imidazolidin-1-ylmethyl)-butyric acid;

(R) 4-Hydroxyimino-4-(6,7,8,9-tetrahydro-5H-fluoren-2-yl)-2-[2-(3,4,4-trimethyl-2,5-dioxo-imidazolidin-1-yl)-ethyl]-butyric acid;

(R) 2-[2-Hydroxyimino-2-(6,7,8,9-tetrahydro-5H-fluoren-2-yl)-ethyl]-5-(3,4,4-trimethyl-2,5-dioxo-imidazolidin-1-yl)-pentanoic acid;

(R) 2-(1,3-Dioxo-1,3-dihydro-isoindol-2-ylmethyl)-4-oxo-4-(6,7,8,9-tetrahydro-5H-fluoren-2-yl)-butyric acid;

(R) 2-[2-(1,3-Dioxo-1,3-dihydro-isoindol-2-yl)-ethyl]4-oxo-(6,7,8,9-tetrahydro-5H-fluoren-2-yl)-butyric acid;

(R) 5-(1,3-Dioxo-1,3-dihydro-isoindol-2-yl)-2-[2-oxo-2-(6,7,8,9-tetrahydro-5H-fluoren-2-yl)-ethyl]-pentanoic acid;

(R) 2-(1,3-Dioxo-1,3-dihydro-isoindol-2-ylmethyl)-4-hydroxyimino-4-(6,7,8,9-tetrahydro-5H-fluoren-2-yl)-butyric acid;

(R) 2-[2-(1,3-Dioxo-1,3-dihydro-isoindol-2-yl)-ethyl]-4-hydroxyimino-4-(6,7,8,9-tetrahydro-5H-fluoren-2-yl)-butyric acid;

(R) 5-(1,3-Dioxo-1,3-dihydro-isoindol-2-yl)-2-[2-Hydroxyimino-2-(6,7,8,9-tetrahydro-5H-fluoren-2-yl)-ethyl]-pentanoic acid;

(R) 4-Oxo-2-phenethyl(6,7,8,9-tetrahydro-5H-10-oxa-benzo[a]azulen-2-yl)-butyric acid;

(R) 2-[2-Oxo-2-(6,7,8,9-tetrahydro-5H-10-oxa-benzo[a]azulen-2-yl)-ethyl]-5-phenyl-pentanoic acid;

(R) 2-[2-Oxo-2-(6,7,8,9-tetrahydro-5H-10-oxa-benzo[a]azulen-2-yl)-ethyl]-6-phenyl-hexanoic acid;

(R) 2-[2-Oxo-2-(6,7,8,9-tetrahydro-5H-10-oxa-benzo[a]azulen-2-yl)-ethyl]-7-phenyl-heptanoic acid;

(R) 2-[2-Oxo-2-(6,7,8,9-tetrahydro-5H-10-oxa-benzo[a]azulen-2-yl)-ethyl]-8-phenyl-octanoic acid;

(R) 4-Hydroxyimino-2-phenethyl-4-(6,7,8,9-tetrahydro-5H-10-oxa-benzo[a]azulen-2-yl)-butyric acid;

(R) 2-[2-Hydroxyimino-2-(6,7,8,9-tetrahydro-5H-10-oxa-benzo[a]azulen-2-yl)-ethyl]-5-phenyl-pentanoic acid;

(R) 2-[2-Hydroxyimino-2-(6,7,8,9-tetrahydro-5H-10-oxa-benzo[a]azulen-2-yl)-ethyl]-6-phenyl-hexanoic acid;

(R) 2-[2-Hydroxyimino-2-(6,7,8,9-tetrahydro-5H-10-oxa-benzo[a]azulen-2-yl)-ethyl]-7-phenyl-heptanoic acid;

(R) 2-[2-Hydroxyimino-2-(6,7,8,9-tetrahydro-5H-10-oxa-benzo[a]azulen-2-yl)-ethyl]-8-phenyl-octanoic acid;

(R) 4-Oxo-4-(6,7,8,9-tetrahydro-dibenzothiophen-3-yl)-2-(3,4,4-trimethyl-2,5-dioxo-imidazolidin-1-ylmethyl)-butyric acid;

(R) 4-Oxo-4-(6,7,8,9-tetrahydro-dibenzothiophen-3-yl)-2-[2-(3,4,4-trimethyl-2,5-dioxo-imidazolidin-1-yl)ethyl]-butyric acid;

(R) 2-[2-Oxo-2-(6,7,8,9-tetrahydro-dibenzothiophen-3-yl)-ethyl]-5-(3,4,4-trimethyl-2,5-dioxoimidazolidin-1-yl)-pentanoic acid;

(R) 4-Hydroxyimino-4-(9-methyl-6,7,8,9-tetrahydro-5H-carbazol-2-yl)-2-phenethyl-butyric acid;

(R) 2-[2-Hydroxyimino-2-(9-methyl-6,7,8,9-tetrahydro-5H-carbazol-2-yl)-ethyl]-5-phenyl-pentanoic acid;

(R) 2-[2-Hydroxyimino-2-(9-methyl-6,7,8,9-tetrahydro-5H-carbazol-2-yl)-ethyl]-6-phenyl-hexanoic acid;

(R) 2-[2-Hydroxyimino-2-(9-methyl-6,7,8,9-tetrahydro-5H-carbazol-2-yl)-ethyl]-7-phenyl-heptanoic acid;

(R) 2-[2-Hydroxyimino-2-(9-methyl-6,7,8,9-tetrahydro-5H-carbazol-2-yl)-ethyl]-8-phenyl-octanoic acid;

(R) 4-Hydroxyimino-4-(6,7,8,9-tetrahydro-dibenzothiophen-3-yl)-2-(3,4,4-trimethyl-2,5-dioxo-imidazolidin-1-ylmethyl)-butyric acid;

(R) 4-Hydroxyimino-4-(6,7,8,9-tetrahydro-dibenzothiophen-3-yl)-2-[2-(3,4,4-trimethyl-2,5-dioxo-imidazolidin-1-yl)-ethyl]-butyric acid;

(R) 2-[2-Hydroxyimino-2-(6,7,8,9-tetrahydro-dibenzothiophen-3-yl)-ethyl]-5-(3,4,4-trimethyl-2,5-dioxo-imidazolidin-1-yl)-pentanoic acid;

(R) 4-(9-Methyl-6,7,8,9-tetrahydro-5H-carbazol-2-yl)-4-oxo-2-phenethyl-butyric acid;

(R) 2-[2-(9-Methyl-6,7,8,9-tetrahydro-5H-carbazol-2-yl)-2-oxo-ethyl]-5-phenyl-pentanoic acid;

(R) 2-[2-(9-Methyl-6,7,8,9-tetrahydro-5H-carbazol-2-yl)-2-oxo-ethyl]-6-phenyl-hexanoic acid;

(R) 2-[2-(9-Methyl-6,7,8,9-tetrahydro-5H-carbazol-2-yl)-2-oxo-ethyl]-7-phenyl-heptanoic acid; and (R) 2-[2-(9-Methyl-6,7,8,9-tetrahydro-5H-carbazol-2-yl)-2-oxo-ethyl]-8-phenyl-octanoic acid; and corresponding isomers thereof; or a pharmaceutically acceptable salt thereof.

The compounds of Formula I are valuable inhibitors of a number of different matrix metalloproteinases. It has been shown previously that inhibitors of matrix metalloproteinases have efficacy in models of disease states like arthritis and metastasis that depend on modification of the extracellular matrix.

In vitro experiments were carried out which demonstrate the efficacy of compounds of Formula I as potent and specific inhibitors of a variety of matrix metalloproteinases. Experiments were carried out with the full-length and catalytic domains of the proteinases. Table 1 shows the activity of Examples 1–2 versus MMP-1FL (collagenase-1 full length enzyme), MMP-2CD (gelatinase A catalytic domain), MMP-2FL (gelatinase A full length enzyme), MMP-3CD (stromelysin-1 catalytic domain), MMP-7FL (matrilysin full length enzyme), MMP-9-FL (gelatinase B full length enzyme), MMP-13CD (collagenase-3 catalytic domain), and MMP-14CD (membrane-type MMP-1). $IC_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli*," Biochemistry, 1992;31:11231–11235; Ye Q.-Z., Johnson L. L., Yu A. E., and Hupe D., "Reconstructed 19 kDa catalytic domain of gelatinase A is an active proteinase," *Biochemistry*, 1995;34:4702–4708.) MMP-13CD was expressed from a synthetic gene and purified from *Escherichia coli* cell culture according to a previously described method (Ye Q.-Z., Johnson L. L., and Baragi V., "Gene synthesis and expression in *E. coli* for PUMP, a human matrix metalloproteinase," *Biochemical and Biophysical Research Communications*, 1992; 186:143–149).

TABLE 1

Biological Activity of Compounds of Formula I

| | $IC_{50}$ ($\mu$M) | | | | | | | |
|---|---|---|---|---|---|---|---|---|
| Example | MMP-1FL | MMP-2CD | MMP-2FL | MMP-3CD | MMP-7FL | MMP-9FL | MMP-13CD | MMP-14CD |
| 1 | 100 | 0.01835 | 0.0595 | 0.1145 | 100 | 32 | 1.206667 | 0.24 |
| 2 | 67 | 0.096 | 0.445 | 0.13 | 84 | 100 | 9.7 | 0.82 |
| 3 | 31 | 0.0585 | 0.945 | 0.315 | 86 | 14 | 1.42 | 2 |

The following list contains abbreviations and acronyms used within the schemes and text:

| | |
|---|---|
| GBM | Glomerular basement membrane |
| ECM | Extracellular matrix |
| CNS | Central nervous system |
| $CH_2Cl_2$ | Dichloromethane |
| EAE | Experimental autoimmune encephalomyelitis |
| MMP | Matrix metalloproteinase |
| TIMPs | Tissue inhibitors of matrix metalloproteinases |
| VSMC | Vascular smooth muscle cell |
| TFA | Trifluoroacetic acid |
| $IC_{50}$ | Concentration of compound required to inhibit 50% of enzyme activity |
| HCl | Hydrogen chloride |
| THF | Tetrahydrofuran |
| Pd | Palladium |
| Na | Sodium |
| NaH | Sodium hydride |
| LiOH | Lithium hydroxide |
| LiCl | Lithium Chloride |
| $H_2O$ | Water |
| $H_2$ | Hydrogen |
| CDI | 1,1'-Carbonyldiimidazole |
| hv | light |
| $SO_3$.DMF | Sulfur trioxide dimethyl formamide |
| $SOCl_2$ | Thionyl Chloride |
| t-Bu | tertiary butyl |
| BOC | tertiary butoxycarbonyl |

-continued

| | |
|---|---|
| LDA | Lithium diisopropylamide |
| MeOH | Methanol |
| DMF | Dimethylformamide |
| p-TsOH(p-TSA) | para-Toluenesulfonic acid |
| CHCl$_3$ | Chloroform |
| CDCl$_3$ | Deuterated chloroform |
| E | Entgegen |
| Z | Zusammen |
| H$_2$NOBz | O-Benzyl hydroxylamine |
| TEA, Et$_3$N | Triethylamine |
| CH$_3$CN | Acetonitrile |
| DBU | 1,8-Diazabicyclo[5.4.0]undec-7-ene |
| DCC | Dicyclohexylcarbodiimide |
| PPA | Polyphosphoric acid |
| BaSO$_4$ | Barium sulfate |
| DMSO-d$_6$ | Deuterated dimethylsulfoxide |
| MgSO$_4$ | Magnesium sulfate |
| 1H-NMR | Proton nuclear magnetic resonance |
| PPM | Parts per million |
| MS | Mass spectrum |
| CI-MS | Chemical ionization mass spectrum |
| NaNO$_2$ | Sodium nitrite |
| KBr | Potassium bromide |
| N$_2$ | Nitrogen |
| AlCl$_3$ | Aluminum chloride |
| ZnCl$_2$ | Zinc chloride |
| SnCl$_2$ | Stannous chloride |
| FeCl$_3$ | Ferric chloride |
| ClCH$_2$CH$_2$Cl(DCE) | Dichloroethane |
| H$_2$S | Hydrogen sulfide |
| NaOAc | Sodium acetate |
| KHMDS | Potassium hexamethyldisilazide |
| NBS | N-bromosuccinimide |
| PG | Protecting group |
| CCl$_4$ | Carbon tetrachloride |
| NFSl | N-Fluorobenzenesulfonimide |
| EtOH | Ethanol |
| (COCl)$_2$ | Oxalyl chloride |
| Et$_3$SiH | Triethylsilane |
| Lawesson's reagent | [2,4-bis(4-methoxyphenyl)-1,3-dithia-2,4-diphosphetane-2,4-disulfide] |
| DAST | Diethylaminosulfur trifluoride |
| KOH | Potassium hydroxide |
| NaBH$_4$ | Sodium borohydride |
| TMS-Cl | Chlorotrimethylsilane |
| i-C$_4$H$_9$OCOCl | Isobutyl chloroformate |

Tricyclic aryl and tricyclic heteroaryl starting materials of formula (3)

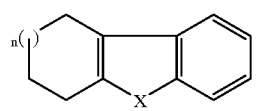

(3)

wherein n is zero or an integer of 1 or 2; and

X is —O—,

—S(O)$_p$— wherein p is zero or an integer of 1 or 2,

wherein R$^6$ is hydrogen, alkyl, acyl, or benzyl,

—CH$_2$—, or

are either obtained from commercial sources (X=N-R$^6$ wherein R$^6$ is as defined above) or prepared using methods known in the art, e.g., Bachelet J. P. and Caubere P., *J. Org. Chem.*, 1982;47:234–238; Ebel F., *Helv. Chim. Acta*, 1929;12:3–16; Vanrysselberghe V. et al., *Ind. Eng. Chem. Res.*, 1996;35:3311–3318; Derouane D. et al.,*J. Chem. Soc., Chem. Commun.*, 1995;10:993–994; Miki Y. and Sugimoto Y., Seikiyu Gakkaishi, 1994;37:386–394; Miki Y. et al., Seikiyu Gakkaishi, 1992;35:332–338; Rankel L. A., *Fuel Sci. Technol. Int.*, 1991;9:1435–1447; Siskin M. et al., *Energy Fuels*, 1990;4:482–488; Sundaram K. M. et al., *Chem. Eng. Commun.*, 1988;71:53–71; Francisco M. A. et al., *J. Org. Chem.*, 1988;53:596–600; Nagai M. et al., *J. Catal.*, 1986;97:52–58; Miyake M. et al., *Bull Chem. Soc. Japan*, 1979;52:559–563; Ando W. et al., *J. Chem. Soc. Chem. Commun*, 1975;17:704–705; Fraser P. S. et al., *J. Org. Chem.*, 1974;39:2509–2513; Cagniant P. et al., *Bull. Soc. Chim. Fr.*, 1969;2:607–612; and Cagniant D. et al., *Bull. Soc. Chim. Fr.*, 1969;2:601–606; U.S. Pat. Nos. 5,721,185, 5,670,680; International Published Patent Application WO 95/27717; Smith W. et al., *J. Org. Chem.*, 1990;55:5301–5302; Mejer S., *Pol. of Chem.*, 1979;53:2385–2388; Canonne P. et al., *J. Org. Chem.*, 1980;45:1828–1835; Parham W. E., Synthesis, 1976;116–117; Japanese Patent Application JP 08191063 A2; Parhan W. E., *J. Org. Chem.*, 1969;34:1899–1904; McClure K. F. et al., *Bioorg. Med Chem. Lett.*, 1998;8:143–146.

The synthesis of starting materials for a compound of Formula I wherein X is —O— is shown in Scheme 1 (Ebel's method). Thus, a compound of formula (1) wherein n is zero or an integer of 1 or 2 is reacted with phenol in the presence of sodium, or sodium hydride and the like in the presence of a solvent such as benzene, tetrahydrofuran and the like to afford a compound of formula (2). Cyclization of a compound of formula (2) in the presence of an acid such as, for example, polyphosphoric acid, para-toluenesulfonic acid and the like in the presence of a solvent such as benzene and the like affords a compound of formula (3). Ebel's method for the synthesis of 1,2,4,4-tetrahydrodibenzofuran (3, n=1) was applied to the synthesis of 2,3-dihydro-1H-8-oxa-cyclopenta[a]indene (3, n=0).

The synthesis of compounds of Formula I where Z is CO, X is O, S(O)$_p$, CH$_2$, CO, NR$^6$, R$^5$ is OH, SH, and R$^1$, R$^2$, R$^3$, and R$^4$ and n are as defined above, can be made by the route shown in Scheme 2. The heterocycle (4) is acylated using Friedel-Crafts conditions with a compound of formula (6), prepared according to known methods such as, for example, as reported by Beckett et al., *Synlett.*, 1993:137, or the corresponding anhydride of formula (5) in the presence of a Lewis acid such as, for example, FeCl$_3$, AlCl$_3$, ZnCl$_2$, SnCl$_4$, and the like either neat or in an inert solvent such as dichloromethane, 1,2-dichloroethane, nitrobenzene, and the like at about −40° C. to about 120° C. to give a compound of formulas (7 and 8). A compound of formula (7) can be deprotected using standard methodology known to one skilled in the art to give the corresponding carboxylic acid (8), which can then be condensed with R$^7$NH$_2$ to give a compound of formula (9). Alternatively, the carboxylic acid can be coupled with hydrogen sulfide after pretreatment with a suitable coupling agent such as, for example, 1,1'-carbonyldiimidazole (CDI), dicyclohexylcarbodiimide (DCC), and the like, and then condensed with $R^7NH_2$ to give a compound of formula (12). Compound (9) can be treated with a protected hydroxylamine derivative such as O-benzylhydroxylamine to give the protected hydroxamic acid derivative (10). This can be deprotected by hydrogenolysis using a catalyst, such as palladium/$BaSO_4$ and hydrogen gas to give the hydroxamic acid (11).

The synthesis of compounds of Formula I where $R^2$ and $R^4$ are hydrogen, Z is CO, X is O, $S(O)_p$, $CH_2$, CO, $NR^6$, $R^5$ is OH, SH, and $R^1$ and $R^3$ and n are as defined above, can be made by the route shown in Scheme 3.

In Scheme 3, (R)- or (S)-4-benzyl-2-oxazolidinone can be reacted with an acid chloride (13), prepared using standard methodology known to one skilled in the art, in the presence of a non-nucleophilic base such as, for example, sodium hydride and the like in an inert solvent such as, for example, tetrahydrofuran and the like at temperatures between about –40° C. and about reflux to give the N-acyl-oxazolidinone (14). The N-acyl-oxazolidinone (14) can be reacted with a suitable base such as, for example, potassium hexamethyl-disilazide (KHDMS), lithium diisopropylamide (LDA), and the like followed by a bromoester (15), prepared in racemic form by brorination of the corresponding ester (16) with a suitable brominating reagent such as, for example, N-bromosuccinimide (NBS) and the like in a suitable solvent such as, for example, carbon tetrachloride and the like in the presence of ultraviolet light and a peroxide such as, for example, benzoyl peroxide and the like or in chiral form by reaction of an amino acid (17) with sodium nitrite and potassium bromide in aqueous hydrobromic acid followed by reacting the resulting bromoacid with a suitable coupling agent such as, for example, CDI, DCC, i-$C_4H_9OCOCl$, and the like and reacting the activated acid with a suitable alcohol such as, for example, methanol, ethanol, benzyl alcohol, and the like to give a compound of formula (18). A compound of formula (18), which may exist as a mixture of diastereoisomers, can be purified by a suitable technique such as, for example, chromatography on silica gel, and the like to give pure stereoisomers (PG=t-Bu or $CH_2Ph$), which can be reacted with lithium hydroxide in THF-water followed by reaction of the resulting carboxylic acid with oxalyl chloride to give the corresponding acid chloride (19).

The acid chloride (19) is then reacted with a heterocycle of formula (4) using Friedel-Crafts conditions (as previously described) to give compound (20), which can be deprotected using methods known in the art to give compounds of formula (21).

The synthesis of compounds of Formula I where $R^1$, $R^2$, $R^3$ (or $R^4$) are hydrogen, Z is CO, X is O, $S(O)_p$, $CH_2$, CO, $NR^6$, $R^5$ is OH, and $R^4$ (or $R^3$) and n are as defined above, can be made by the route shown in Scheme 4. Friedel-Crafts acylation, in the presence of a Lewis acid such as, for example, $FeCl_3$, $AlCl_3$, $ZnCl_2$, $SnCl_4$, and the like either neat or in an inert solvent such as dichloromethane, 1,2-dichloroethane, nitrobenzene, and the like at about –40° C. to about 120° C., of the heterocycle (4) with bromoacetyl bromide gives compound (22). This is then condensed with the enolate of dimethyl malonate (generated by treating dimethyl malonate with a metal hydride, such as sodium hydride, in a solvent such as THF or dimethyl ether at temperatures ranging from –10° C. to about 40° C.) to yield compound (23). This can be alkylated by deprotonation with a metal hydride, such as sodium hydride, in a solvent such as DMF at temperatures ranging from –10° C. to about 40° C. followed by treatment with an alkylating agent ($R^{3(4)}X$) to yield compound (24). Hydrolysis of the ester groups can be achieved by treatment with lithium hydroxide in a solvent such as dioxane at temperatures ranging from –10° C. to about 40° C. to give the corresponding diacid (25). Decarboxylation occurs by heating compound (25) in a solvent such as toluene with a base such as triethylamine, to give compound (26) which can then be condensed with $R^7NH_2$ to give a compound of formula (27).

Alternatively, as shown in Scheme 5, esters (28) can be alkylated by treatment with a base, such as lithium diisopropylamide in a solvent such as THF or dimethyl ether at temperatures ranging from –80° C. to about 10° C., and tert-butyl bromoacetate (29) to give the diester (30). This could be selectively deprotected using trifluoroacetic acid in the presence of a suitable carbonium ion scavenger such as, for example, anisole, thioanisole, triethylsilane, and the like in a solvent such as dichloromethane, chloroform, and the like, to give the ester acid (31). This can then be converted to the corresponding acid chloride (32) by treatment with a chlorinating agent such as oxalyl chloride or thionyl chloride in a solvent such as dichloromethane. Friedel-Crafts acylation, in the presence of a Lewis acid such as, for example, $FeCl_3$, $AlCl_3$, $ZnCl_2$, $SnCl_4$, and the like either neat or in an inert solvent such as dichloromethane, 1,2-dichloroethane, nitrobenzene, and the like at about –40° C. to about 120° C., of the heterocycle (4) with (32) gives compound (33). The ethyl ester is hydrolyzed by treatment with lithium hydroxide in a solvent such as dioxane at temperatures ranging from –10° C. to about 40° C. to give the corresponding acid (34) which can then be condensed with $R^7NH_2$ to give a compound of formula (35).

Alternatively, compounds of Formula I wherein Z is

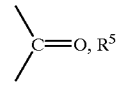

is OH or SH, and $R^1$, $R^2$, $R^3$, $R^4$, X and n are as defined in Formula I, can be synthesized according to the sequence outlined in Scheme 6.

In Scheme 6 the heterocycle (4), prepared according to the procedure outlined in Scheme 1, is allowed to react with a suitable acylating agent such as, for example, the acid chloride of formula (13) and the like in the presence of a Lewis acid such as, for example, $FeCl_3$, $AlCl_3$, $ZnCl_2$, and the like either neat or in an inert solvent such as, for example, dichloromethane, nitrobenzene, and the like at about –40° C. to about 120° C. to give a compound of formula (36). A compound of formula (36) is allowed to react with a suitable strong base such as, for example, n-butyl lithium, lithium diisopropylamide, potassium hexamethyl-disilazide, and the like in an inert solvent such as, for example, tetrahydrofuran, dimethyl ether, and the like at about –78° C. to about 25° C. followed by a suitable alkylating agent of formula (37), or N-fluorodibenzenesulfonamide (NFSI) for $R^2$ equals fluorine, at temperatures at about –78° C. to about 50° C. to give a compound of formula (38). A compound of formula (38) is allowed to react with a suitable strong base such as, for example, n-butyl lithium, lithium diisopropylamide, potassium hexamethyldisilazide, and the like in an inert solvent such as, for example, tetrahydrofuran, dimethyl ether, and the like at about –78° C. to about 25° C. followed by a suitable alkylating agent of formula (39) to give a compound of formula (40). A compound of formula (40) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of formula (41). A compound of formula (41) is condensed with $R^7NH_2$ to give a compound of formula (42). Alternatively, a compound of formula (41) is allowed to react with hydrogen sulfide after pretreatment with a suitable coupling agent such as, for example, 1,1'-carbonyldiimidazole, N,N'-dicyclohexylcarbodiimide, isobutyryl chloride, and the like, and then condensed with R⁷NH₂ to give a compound of formula (43).

Alternatively, a compound of formula (40) is allowed to react with a suitable base such as, for example, n-butyl lithium, lithium diisopropylamide, potassium hexamethyldisilazide, and the like in an inert solvent such as, for example, tetrahydrofuran, dimethyl ether, and the like at about −78° C. to about 25° C. followed by a suitable alkylating agent of formula (44) or NFSI for R³ equals fluorine, at temperatures at about −78° C. to about 50° C. to give a compound of formula (45). A compound of formula (45) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of formula (46). A compound of formula (46) is converted to compounds of formulas (47) and (48) according to the procedure described for the conversion of a compound of formula (41) to compounds of formulas (42) and (43), respectively. Alternatively, a compound of formula (45) is allowed to react with a suitable base such as, for example, n-butyl lithium, lithium diisopropylamide, potassium hexamethyldisilazide, and the like in an inert solvent such as, for example, tetrahydrofuran, dimethyl ether, and the like at about −78° C. to about 25° C. followed by a suitable alkylating agent of formula (49) or NFSI for R⁴ equals fluorine, at temperatures at about −78° C. to about 50° C. to give a compound of formula (50). A compound of formula (50) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of formula (51). A compound of formula (51) is converted to compounds of formulas (52) and (53) according to the procedure described for the conversion of a compound of formula (41) to compounds of formulas (42) and (43), respectively.

Alternatively, compounds of Formula I wherein Z is

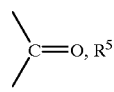

is OH or SH, and, R¹, R², R³, R⁴, X, and n are as defined in Formula I are synthesized according to the sequence outlined in Scheme 7.

In Scheme 7, a compound of formula (54) is allowed to react with a suitable base such as, for example, n-butyl lithium, lithium diisopropylamide, potassium hexamethyldisilazide, and the like in an inert solvent such as, for example, tetrahydrofuran, dimethyl ether, and the like at about −78° C. to about 25° C. followed by a suitable alkylating agent of formula (44) or NFSI for R³ equals fluorine, at temperatures at about −78° C. to about 50° C. to give a compound of formula (55). A compound of formula (55) is allowed to react with a suitable base such as, for example, n-butyl lithium lithium diisopropylamide, potassium hexamethyldisilazide, and the like in an inert solvent such as, for example, tetrahydrofliran, dimethyl ether, and the like at about −78° C. to about 25° C. followed by a suitable alkylating agent of formula (56), prepared by allowing a compound of formula (4) to react with a suitable acylating agent such as BrCH₂COCl in the presence of a suitable Lewis acid such as, for example, FeCl₃, AlCl₃, ZnCl₂, and the like either neat or in an inert solvent such as, for example, dichloromethane, nitrobenzene, and the like at about −40° C. to about 120° C., to give a compound of formula (57). A compound of formula (57) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid can be resolved using methods known to one skilled in the art to give a compound of formula (58). A compound of formula (58) is converted to compounds of formulas (59) and (60) according to the procedure described in Scheme 6 for the conversion of a compound of formula (41) to compounds of formulas (42) and (43), respectively. Alternatively, a compound of formula (57) is allowed to react with a suitable base such as, for example, n-butyl lithium, lithium diisopropylamide, potassium hexamethyldisilazide, and the like in an inert solvent such as, for example, tetrahydrofuran, dimethyl ether, and the like at about −78° C. to about 25° C. followed by a suitable alkylating agent of formula (61), or NFSI for R² equals fluorine, at temperatures at about −78° C. to about 50° C. to give a compound of formula (62). A compound of formula (62) is deprotected using appropriate conditions such as, for example, trifluoroacetic acid or anhydrous hydrogen chloride in a suitable solvent such as, for example, dichloromethane or chloroform, with or without a carbomnum ion scavenger such as, for example, triethylsilane, and the resulting carboxylic acid can be resolved using methods known to one skilled in the art to give a compound of formula (63). A compound of formula (63) is converted to compounds of formulas (64) and (65) according to the procedure described in Scheme 6 for the conversion of a compound of formula (41) to compounds of formulas (42) and (43), respectively. Alternatively, a compound of formula (62) is allowed to react with a suitable base such as, for example, n-butyl lithium, lithium diisopropylamide, potassium hexamethyldisilazide, and the like in an inert solvent such as, for example, tetrahydrofuran, dimethyl ether, and the like at about −78° C. to about 25° C. followed by a suitable alkylating agent of formula (66), or NFSI for R¹ equals fluorine, at temperatures at about −78° C. to about 50° C. to give a compound of formula (50). A compound of formula (50) is converted via a compound of formula (51) to compounds of formulas (52) and (53) according to the procedure described in Scheme 6.

Compounds of Formula I wherein Z is CH(OH), C=S, CF₂, or CHF, and R⁵ is OH or SH, and R¹, R², R³, R⁴, X, and n are as defined in Formula I are synthesized according to the sequence outlined in Scheme 8.

In Scheme 8, keto-esters of formulas (7), (40), (45), (50), (57), or (62) can be hydrolyzed to the corresponding keto-acids, such as by stirring in aqueous hydrochloric acid at a concentration between about 2 M and about 6 M and at temperatures between about 25° C. and reflux or by stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification, and the keto-acids can be reduced using an appropriate hydride donating reagent such as sodium borohydride in ethanol, L- or S-selectride and the like in a suitable solvent such as, for example, toluene, tetrahydrofuran and the like to give the alcohol-acid (67). The alcohol-acid (67) can be silylated such as, for example, by allowing it to react with chlorotrimethylsilane (TMS-Cl) in the presence of a catalyst such as, for example, imidazole and the like in a suitable solvent such as, for example, anhydrous dimethylformamide (DMF) and the like to give the corresponding O-silyl alcohol-silyl ester, which can be fluorinated by allowing it to react with a suitable reagent such as, for example, dimethylaminosulfur trifluoride (DAST) and the like in a suitable solvent such as, for example, dichloromethane, chloroform and the like at temperatures between about −20° C. and about reflux to give the corresponding fluoro-silyl ester, which can be hydrolyzed by stirring in aqueous hydrochloric acid at a concentration between about 2 M and about 6 M and at temperatures between about 25° C. and reflux or by stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification or by stirring in the presence of a suitable fluoride reagent such as, for example, tetra-n-butylammonium fluoride, aqueous hydrogen fluoride and the like in a suitable solvent such as, for example, tetrahydrofuran, acetonitrile and the like to give the fluoro-acid (68). The fluoro-acid (68) can be reacted with a suitable coupling agent such as, for example, CDI, DCC, i-$C_4H_9OCOCl$, and the like followed by hydrogen sulfide to give the fluoro-thioacid (69).

Alternatively, the keto-esters of formulas (7), (40), (45), (50), (57), or (62) can be allowed to react with a suitable fluorinating agent such as, for example, DAST and the like in a suitable solvent such as, for example, dichloromethane, chloroform and the like at temperatures between about −20° C. and about reflux to give the corresponding fluoro-ester, which can be hydrolyzed such as by stirring in aqueous hydrochloric acid at a concentration between about 2 M and about 6 M and at temperatures between about 25° C. and reflux or by stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification to give the corresponding difluoro-acid (70). The difluoro-acid (70) can be allowed to react with a suitable coupling agent such as, for example, CDI, DCC, i-$C_4H_9OCOCl$, and the like followed by hydrogen sulfide to give the fluoro-thioacid (71).

Alternatively, keto-esters of formulas (7), (40), (45), (50), (57), or (62) can be hydrolyzed to the corresponding keto-acids, such as by stirring in aqueous hydrochloric acid at a concentration between about 2 M and about 6 M and at temperatures between about 25° C. and reflux or by stirring in the presence of a suitable alkali metal hydroxide such as, for example, lithium, sodium, or potassium hydroxide and the like in a suitable solvent such as, for example, methanol, ethanol, or aqueous THF and the like at temperatures between about 0° C. and reflux followed by acidification, and the keto-acids allowed to react with a suitable sulfur reagent such as, for example, Lawesson's reagent and the like in a suitable solvent such as, for example, tetrahydrofuran and the like at temperatures between about 0° C. and reflux to give the thioketo-acid (72). The thioketo-acid (72) can be allowed to react with a suitable coupling agent such as, for example, CDI, DCC, i-$C_4H_9OCOCl$, and the like followed by hydrogen sulfide to give the thioketo-thioacid (73).

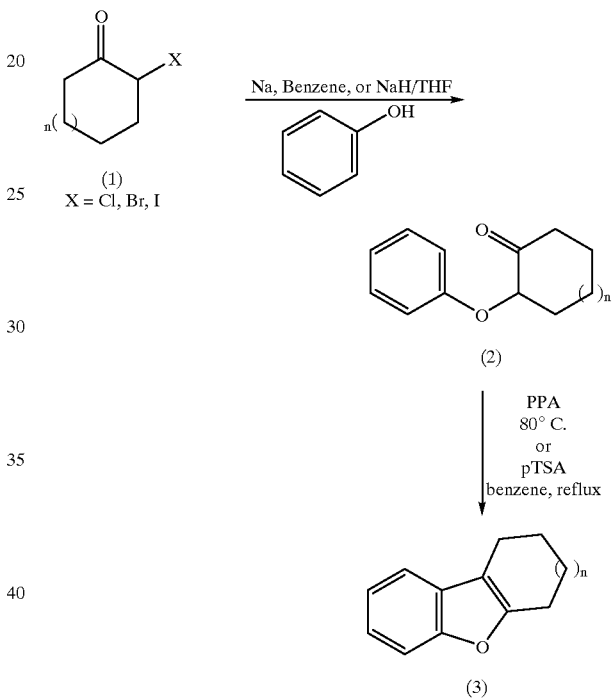

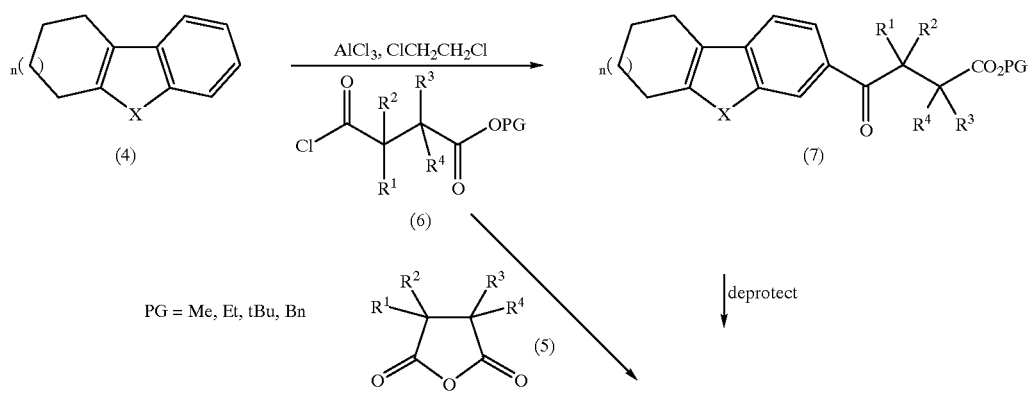

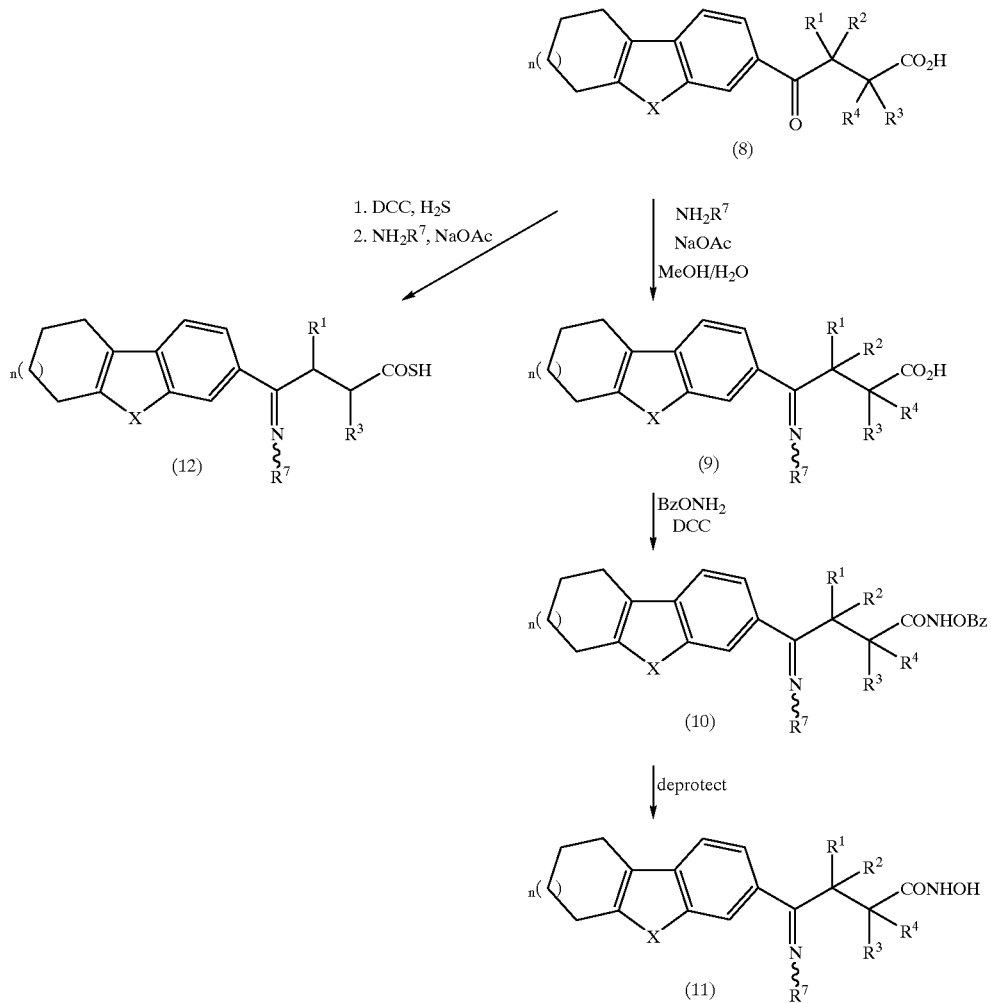
Scheme 3
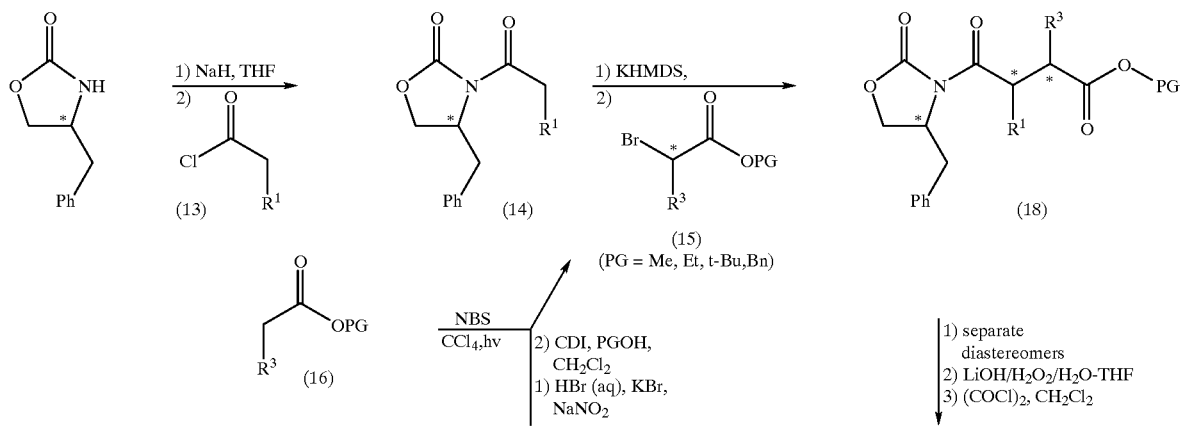

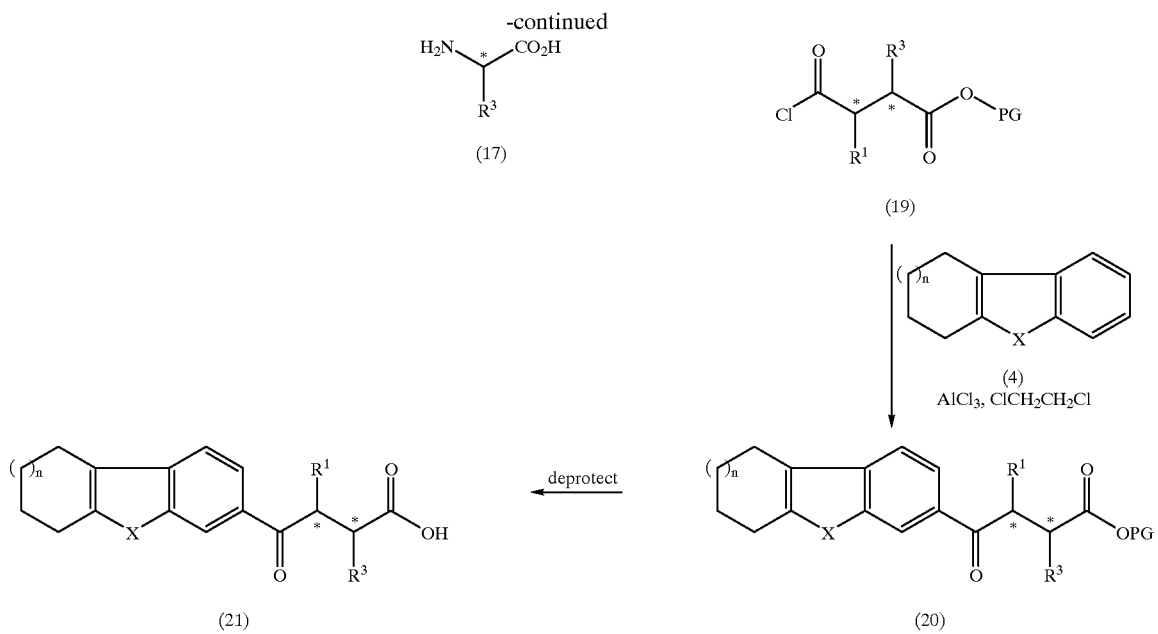
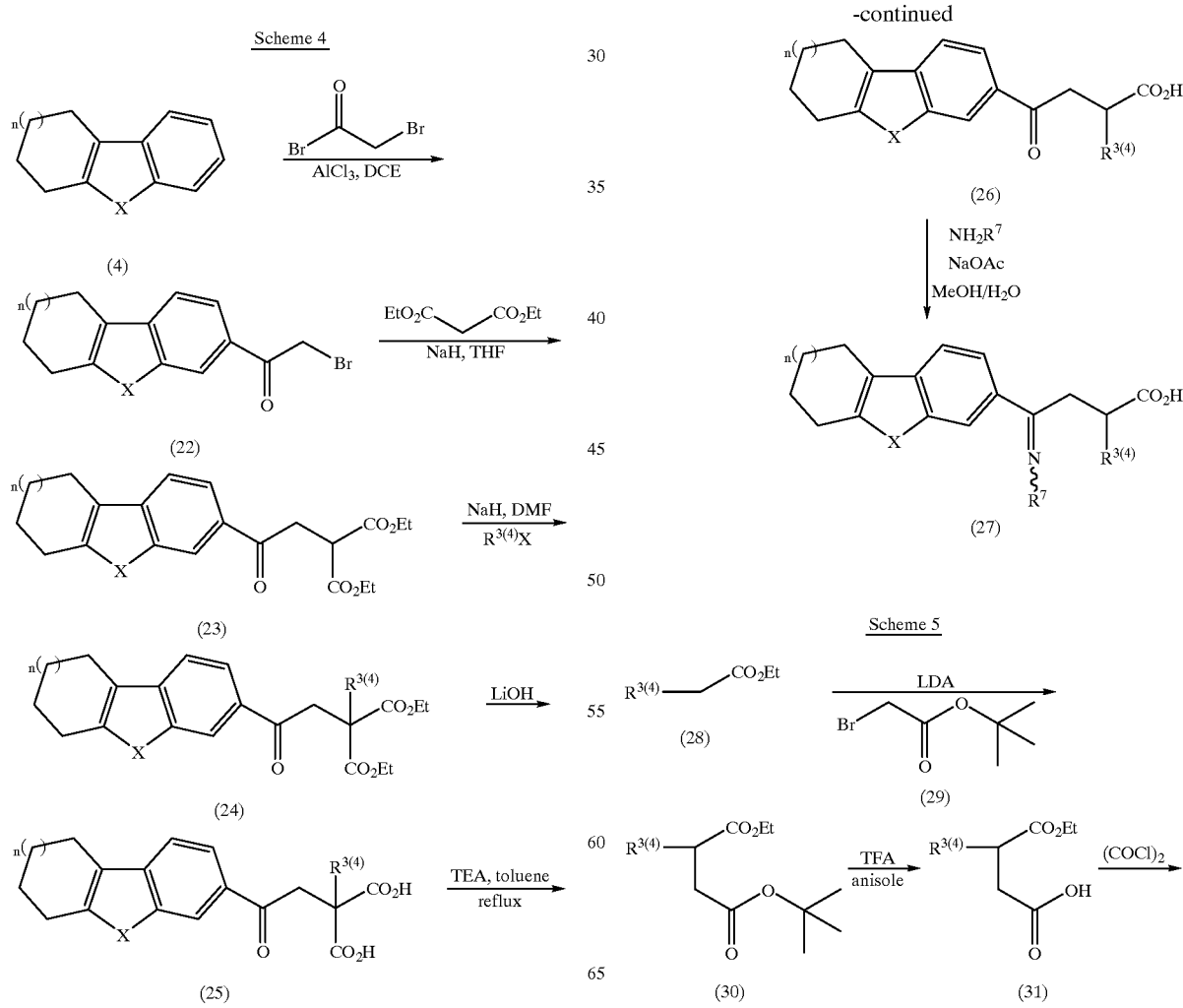

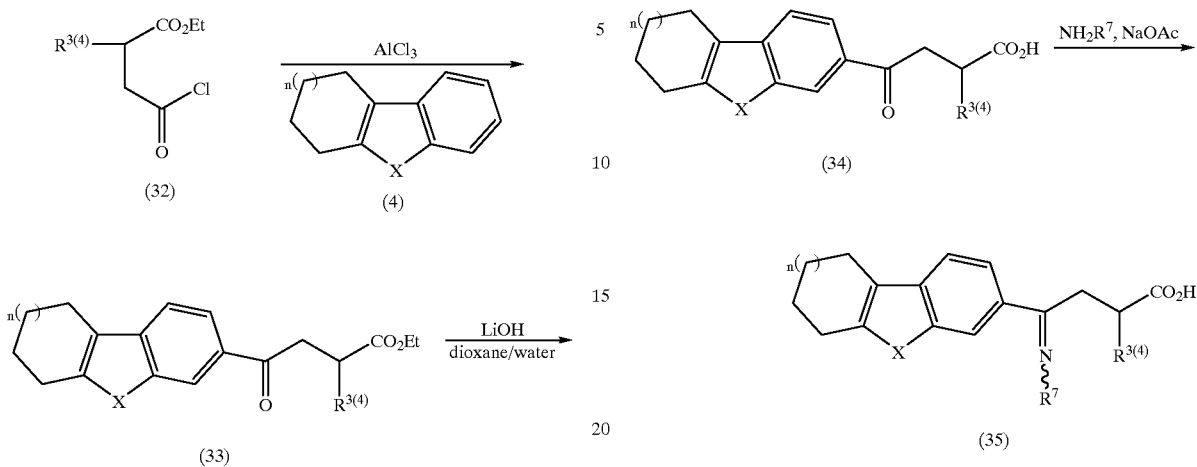
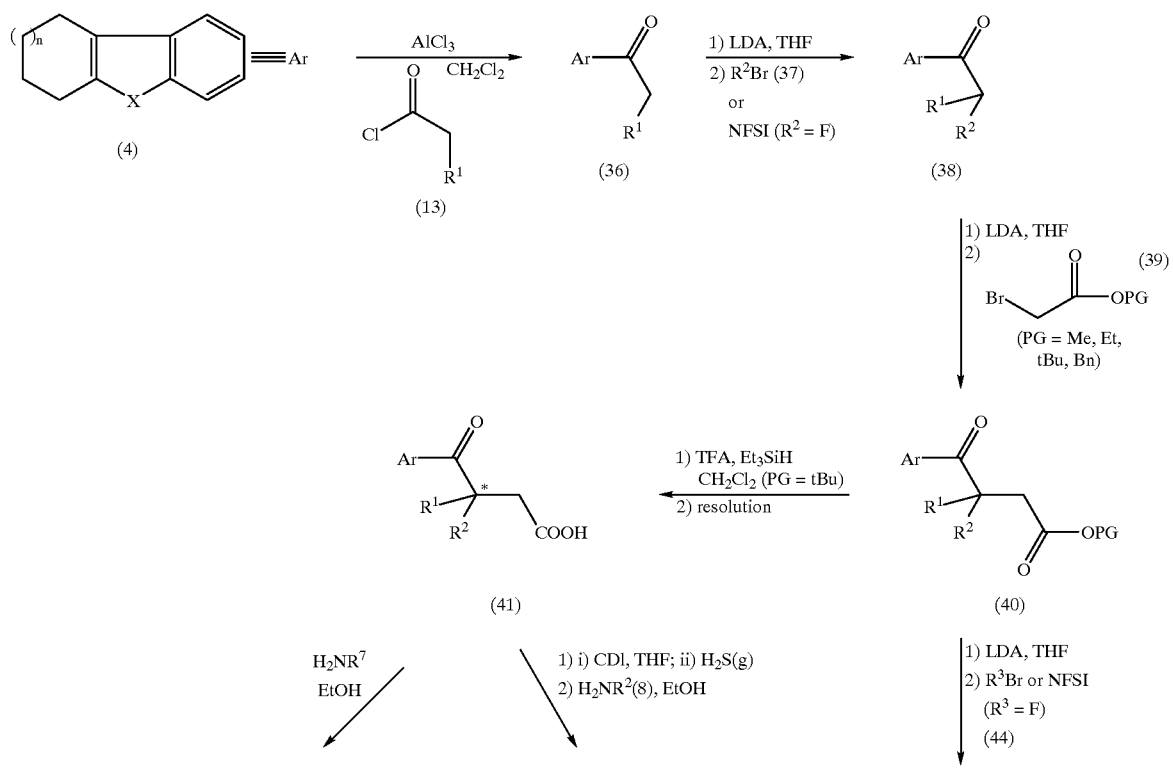
Scheme 6

-continued
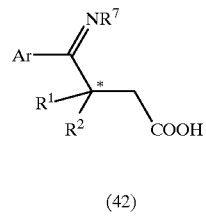
(42)
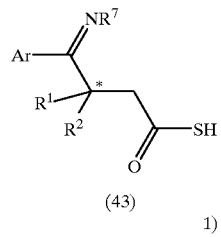
(43)
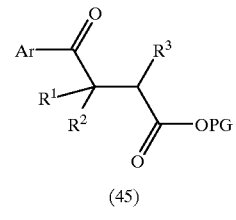
(45)
1) TFA
   Et₃SiH
   CH₂Cl₂
   (PG = tBu)
2) resolution
1) LDA, THF
2) R⁴Br or NFSI
   (R⁴ = F)
   (49)
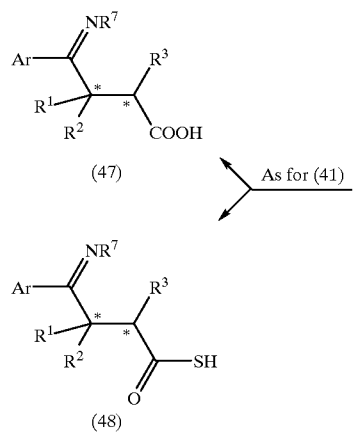
(47)
(48)
As for (41)
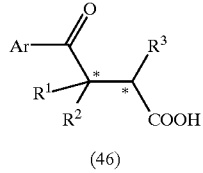
(46)
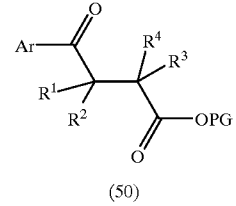
(50)
1) TFA
   Et₃SiH
   CH₂Cl₂
   (PG = tBu)
2) resolution
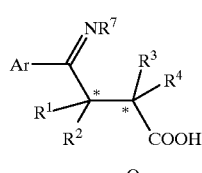
(52)
As for (41)
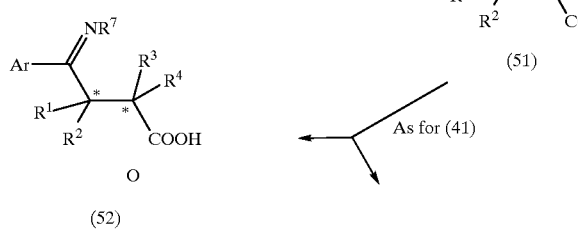
(51)
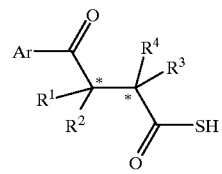
(53)

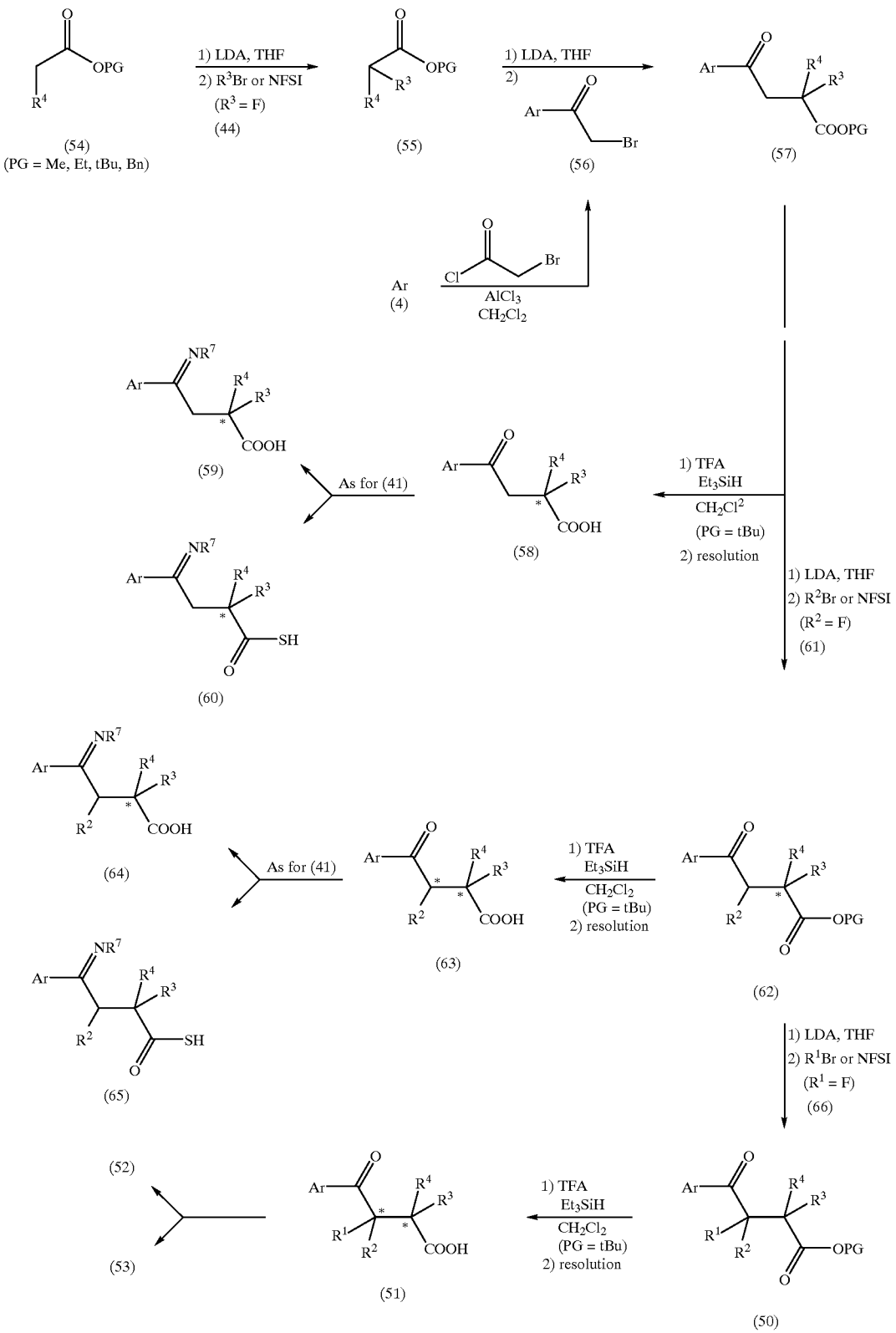

Scheme 8

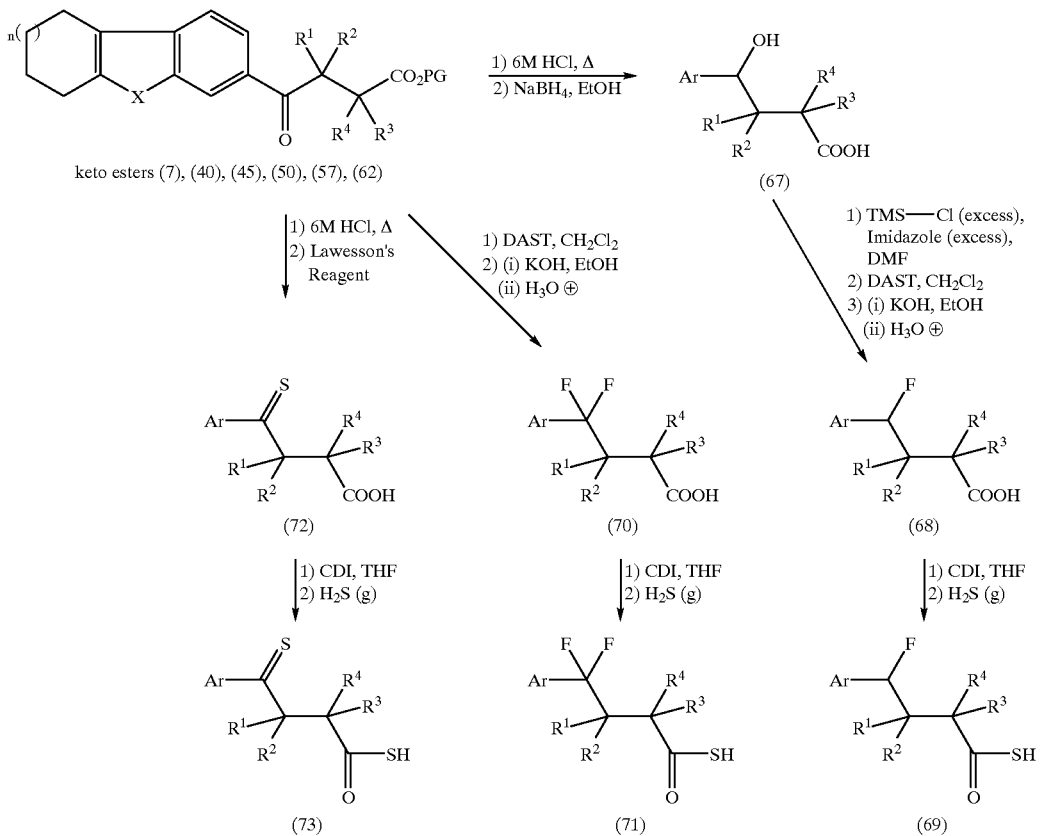

Compounds of formulas 5, 6, 8, 13, 15, 16, 17, 29, 37, 39, 44, or 49 are either commercially available or can be obtained by methods known in the art.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, left ventricular dilation, restenosis, periodontal disease, corneal ulceration, treatment of burns, decubital ulcers, wound healing, cancer, inflammation, pain, arthritis, osteoporosis, renal disease, or other autoimmune or inflammatory disorders dependent upon tissue invasion by leukocytes, or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia grayis, and Duchenne's muscular dystrophy, the compounds utilized in the pharmaceutical methods of the invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optirumw effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

4-Hydroxyimino4-(6,7,8,9-tetrahydro-dibenzofuran-3-yl)-butyric acid

To a methanolic solution (50 mL) of 4-oxo-4-(6,7,8,9-tetrahydro-dibenzofuran-3-yl)-butyric acid (Keumi T., Saga H., Shimakawa S., et al., *Fufui Daigaku, Kogakubu Seni Kogyu Kenkyu Shisetsu Hokoku*, 1976;14:71–7 (mp 143–146° C.; mp 148.5–149.50° C. (lit.)) (0.6 g, 0.0022 mol) and sodium acetate trihydrate (0.9 g, 0.0066 mol) at room temperature with stirring was added an aqueous solution (10 mL) of hydroxylamine hydrochloride (0.31 g, 0.0044 mol). The resulting solution was heated to reflux for 4 hours. The solution was then cooled to room temperature and concentrated in vacuo. The residue was recrystallized form ethyl acetate/hexane (1:1) to yield the title compound (0.32 g, 51%) as a white solid; mp 164° C.

$^1$HNMR (DMSO-$d_6$) δ 7.8 (s, 1H), 7.5 (m, 1H), 7.43 (m, 1H), 2.95 (m, 2H), 2.71 (m, 2H), 2.56 (m, 2H), 1.85 (m, 2H), 1.76 (m, 2H) ppm. MS (m+1) m/z 288.1.

EXAMPLE 2

2-[2-Oxo-2-(6,7,8,9-tetrahydro-dibenzofuran-3-yl)-ethyl]-5-phenyl-pentanoic acid Step (a) Preparation of: 2-(3-Phenyl-propyl)-succinic acid 4-tert-butyl ester 1-ethyl ester To a solution of LDA (10.4 mL, 2 M in heptane/THF) in THF (20 mL), cooled to −70° C. under $N_2$, was added dropwise ethyl 5-phenylvalerate (4 g, 19.4 mmol in 5 mL THF). The dark solution was stirred at −70° C. for 30 minutes, followed by the rapid addition of tert-butyl bromoacetate (4 g, 20.7 mmol in 5 mL THF). The reaction mixture was stirred at −70° C. for 1 hour, then diluted with aqueous HCl (30 mL, 1 M) and ethyl acetate (30 mL). The organic phase was separated, washed with brines dried ($MgSO_4$), and concentrated in vacuo. The resulting liquid was passed through a silica gel column (elution with hexane/ethyl acetate (3:1)) to give the diester as a colorless liquid (2.4 g, 40%).

$^1$HNMR (CDCl$_3$) δ 7.3–7.1 (m, 5H), 4.2–3.8 (m, 3H), 2.6 (m, 2H), 1.6 (m, 4H), 1.4 (s, 9H), 1.2 (m, 5H) ppm.

Step (b) Preparation of: 2-(3-Phenyl-propyl)-succinic acid 1-ethyl ester

To a solution of anisole (0.9 g, 8.3 mmol) in trifluoroacetic acid (10 mL) was added dropwise the diester (2.4 g, 7.8 mmol) prepared in step (a). Hydrolysis of the tert-butyl ester was completed in 4 hours, at which time the solution was poured over ice, and the product was partitioned between dimethyl ether and the aqueous acid. The organic phase was separated, dried ($MgSO_4$), and concentrated in vacuo leaving a viscous liquid. The product was purified using silica gel chromatography (elution with hexanelethyl acetate (3:1)) to give the half-acid ester as a pale orange liquid (0.75 g, 38%).

$^1$HNMR (CDCl$_3$) δ 7.3–7.1 (m, 5H), 4.2 (m, 2H), 2.9–2.4 (m, 5H), 1.6 (m, 4H), 1.3 (m, 3H) ppm.

Step (c) Preparation of: 2-Chlorocarbonylmethyl-5-phenyl-pentanoic acid ethyl ester The acid prepared in step (b) (0.73 g, 2.8 mmol) was diluted with dichloromethane (5 mL) and treated with oxalyl chloride (1.05 g, 8.3 mmol) in one portion. A catalytic amount of DMF was added, and the reaction mixture was stirred at room temperature for 16 hours. The solution was concentrated to dryness leaving an orange liquid (0.7 g, 78%).

$^1$HNMR (CDCl$_3$) δ 7.3–7.1 (m, 5H), 4.2 (m, 2H), 3.3 (m, 1H), 2.9 (m, 2H), 2.6 (t, 2H), 1.6 (m, 4H), 1.3 (t, 3H) ppm.

Step (d) Preparation of: 2-[2-Oxo-2-(6,7,8,9-tetrahydro-dibenzofuran-3-yl)-ethyl]-5-phenyl-pentanoic acid ethyl ester.

To a suspension of AlCl$_3$ (0.28 g, 2.1 mmol) in dichloroethane (10 mL) cooled to 0° C. was added dropwise tetrahydro-dibenzofuran (0.30 g, 1.7 mmol). The reaction mixture was stirred for 15 minutes, followed by the addition of the acid chloride (0.5 g, 1.7 mmol) prepared in step (c). After stirring at room temperature for 16 hours, the reaction mixture was poured over ice and diluted with ethyl acetate (50 mL). The organic phase was separated, washed with brine, dried (MgSO$_4$), and concentrated to dryness. The resulting viscous liquid was filtered through a pad of silica gel (elution with hexane/ethyl acetate (9:1)) to yield a yellowish green liquid (0.37 g, 51%).

$^1$HNMR (CDCl$_3$) δ 8.0 (d, 1H), 7.9 (m, 1H), 7.4 (m, 1H), 7.3–7.1 (m, 5H), 4.2 (q, 2H), 3.5 (m, 1H), 3.1–2.9 (m, 2H), 2.8–2.5 (m, 6H), 2.0–1.6 (m, 8H), 1.2 (t, 3H) ppm.

Step (e) Preparation of: 2-[2-Oxo-2-(6,7,8,9-tetrahydro-dibenzofuran-3-yl)-ethyl]-5-pentanoic acid The ester prepared in step (d) (0.36 g, 0.87 mmol) was suspended in p-dioxane/water (5 mL, 1:1) and treated with LiOH (0.091 g) in one portion. The reaction mixture was stirred at room temperature for 16 hours, followed by dilution with aqueous HCl (1 M, pH=1). The product was partitioned between ethyl acetate and the aqueous acid, the organic phase separated, washed with brine, dried (MgSO$_4$), and concentrated in vacuo. The crude product was purified using silica gel chromatography (elution with hexane/ethyl acetate (3:1)) to give the title compound as a white solid (0.075 g, 22%); mp 142–144° C.

$^1$HNMR (CDCl$_3$) δ 8.0 (s, 1H), 7.8 (d, 1H), 7.4 (d, 1H), 7.3 (m, 3H), 7.1 (m, 2H), 3.5 (m, 1H), 3.2 (m, 2H), 2.8–2.6 (m, 6H), 2.0–1.6 (m, 8H) ppm.

EXAMPLE 3

4-Oxo-4-(6,7,8,9-tetrahydro-dibenzofuran-3-yl)-2-(3,4,4-trimethyl-2,5-dioxo-imidazolidin-1-ylmethyl)-butyric acid Step (a) Preparation of 2-Bromo-1-(6,7,8,9-tetrahydro-dibenzofuran-3-yl)-ethanone A suspension of AlCl$_3$ (1.2 g, 9 mmol) in dichloroethane (30 mL) was treated with tetrahydro-dibenzofuran (1.2 g, 6.9 mmol) and bromoacetyl bromide (1.7 g, 8.4 mmol), respectively. The reaction mixture was refluxed for 1 hour, cooled to room temperature, and poured over ice. The aqueous suspension was diluted with chloroform, the layers separated, and the organic portion washed with brine, dried (MgSO$_4$), and concentrated to dryness leaving a viscous liquid. The crude product was purified using silica gel chromatography (elution with toluene) to give a pale yellow solid (0.58 g, 29%).

$^1$HNMR (CDCl$_3$) δ 8.1 (d, 1H), 7.9 (m, 1H), 7.5 (m, 1H), 4.5 (d, 2H), 2.8–2.6 (m, 4H), 2.0–1.8 (m, 4H) ppm.

Step (b) Preparation of: 2-[2-Oxo-2-(6,7,8,9 -tetrahydro-dibenzofuran-3-yl)-ethyl]-malonic acid dimethyl ester To a solution of dimethylmalonate (0.28 g, 1.7 mmol) in DMF (10 mL) stirred under an atmosphere of N$_2$ was added Nail over a period of 10 minutes. Dissolution occurred after 15 minutes, at which time the bromoacetyl tetrahydro-dibenzofuran (0.5 g, 1.7 mmol) was a dded in one portion. The yellow solution was stirred at room temperature for 2 hours, then poured into water (150 mL). The product extracted with 2 portions of dimethyl ether, the extracts combined, washed with water, dried (MgSO$_4$), and concentrated in vacuo leaving a viscous liquid. The product was purified using silica gel chromatography (elution with hexane/ethyl acetate (3:1)) to give the malonate derivative as a colorless liquid (0.24 g, 38%).

$^1$HNMR (CDCl$_3$) δ 8.1 (d, 1H), 7.9 (m, 1H), 7.5 (m, 1H), 4.2 (m, 4H), 4.1 (m, 1H), 3.7 (m, 2H), 2.8–2.6 (m, 4H), 2.0–1.8 (m, 4H), 1.3 (m, 6H) ppm.

Step (c) Preparation of: 2-[2-Oxo-2-(6,7,8,9-tetrahydro-dibenzofuran-3-yl)-ethyl]-2-(3,4,4-trimethyl-2,5-dioxo-imidazolidin-1-ylmethyl)-malonic acid dimethyl ester The malonate derivative prepared in step (b) was diluted with DMF (3 mL) and treated with 3-bromomethyl-1,5,5-timethylhydantoin (0.14 g, 0.59 mmol). The solution was stirred at room temperature under N$_2$, followed by the addition of NaH (0.030 g, 0.75 mmol). The solution was stirred for 16 hours, then diluted with water and ethyl acetate. The organic phase was separated and washed with water, dried (MgSO$_4$), and concentrated in vacuo. The liquid was isolated and passed through a silica gel column (elution with hexane/ethyl acetate (3:1)) to yield a white solid (0.050 g, 15%).

$^1$HNMR (CDCl$_3$) δ 8.1 (d, 1H), 7.9 (m, 1H), 7.5 (m, 1H), 4.4 (d, 2H), 4.2 (m, 4H), 3.7 (d, 2H), 2.8 (s, 3H), 2.75–2.6 (m, 4H), 2.0–1.8 (m, 4H), 1.3 (s, 6H) 1.28 (t, 6H) ppm.

Step (d) Preparation of: 2-[2-Oxo-2-(6,7,8,9-tetrahydro-dibenzofuran-3-yl)-ethyl]-2-(3,4,4,-trimethyl-2,5-dioxo-imidazolidin-1-ylmethyl)-malonic acid The compound prepared in step (c) (0.050 g, 0.09 mmol) was diluted with p-dioxane/H$_2$O (3 mL) followed by the addition of LiOH monohydrate (0.095 g) in one portion. The reaction mixture was stirred at room temperature for 16 hours, then acidified (pH=1) using aqueous HCl (1 M). Ethyl acetate was added, the layers separated, and the organic portion dried (MgSO$_4$) and concentrated leaving a white foam. Trituration with hexanelethyl acetate yielded the bis acid as a white solid (0.040 g, 89%).

CI-MS (C$_{24}$H$_{26}$N$_2$O$_8$) [M+H]$^+$470.

Step (e) Preparation of: 4-Oxo-4-(6,7,8,9-tetrahydro-dibenzofuran-3-yl)-2-(3,4,4-trimethyl-2,5-dioxo-imidazolin-1-ylmethyl)-butyric acid The bis acid prepared in step (d) (0.020 g, 0.042 mmol) was suspended in toluene (3 mL) and treated with one equivalent of triethylamine (4.3 mg, 0.042 mmol). The reaction mixture was refluxed for 2 hours, cooled, and concentrated in vacuo. The product was partitioned between ethyl acetate and aqueous HCl (1 M), the layers separated, and the organic portion dried (MgSO$_4$) and concentrated in vacuo. Trituration of the resulting foam with hexane/ethyl acetate (4:1) yielded the title compound (5 mg, 28%) as a cream colored solid.

$^1$HNMR (CDCl$_3$) δ 7.9 (d, 1H), 7.8 (m, 1H), 7.3 (m, 1H), 3.9–3.2 (m, 5H), 2.8 (s, 3H), 2.7–2.5 (m, 4H), 1.9–1.7 (m, 4H), 1.2 (s, 6H) ppm.

What is claimed is:

1. A compound of Formula I

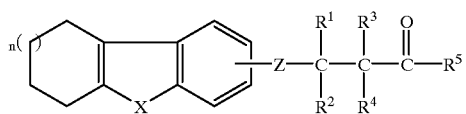

wherein n is an integer of 1 or 2;

X is —O—, or

—S;

Z is

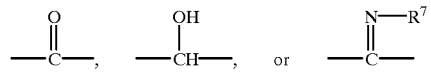

wherein R$^7$ is OR$^8$ wherein R$^8$ is hydrogen, alkyl,

—(CH$_2$)$_m$-aryl wherein m is zero or an integer of 1 to 6,

—(CH$_2$)$_m$-heteroaryl wherein heteroaryl is a 5–6 membered heteroaromatic ring having up to 3 heteroatoms selected from N, O and S, and m is as defined above, —(CH$_2$)$_m$-cycloalkyl having 3–7 carbon atoms in the ring wherein m is as defined above or

wherein R$^9$ and R$^9$a are either the same or different and are hydrogen,
alky of 1–6 carbon atoms,
aryl,
arylalkyl,
heteroaryl, or
cycloalkyl;

R$^1$, R$^2$, R$^3$, and R$^4$ are either the same or different and are
hydrogen,
fluorine,
alkyl,
alkenyl of 2–10 carbon atoms,
alkynyl of 2–10 carbon atoms,
arylalkenyl,
heteroarylalkenyl,
arylalkynyl,
heteroarylalkynyl,
—(CH$_2$)$_m$-aryl wherein m is as defined above,
—(CH$_2$)$_m$-heteroaryl as defined above,
—(CH$_2$)$_m$-cycloalkyl as defined above,
—(CH$_2$)$_q$—X$^a$—(CH$_2$)$_{q^1}$-alkyl wherein X$^a$ is O, S, SO, SO$_2$, or NH, and q and q$^1$ are each zero or an integer of 1 to 6, and the sum of q+q$^1$ is not greater than six,
—(CH$_2$)$_q$—X$^a$—(CH$_2$)$_{q^1}$-aryl wherein X$^a$, q, and q$^1$ are as defined above,
—(CH$_2$)$_q$—X$^a$—(CH$_2$)$_{q^1}$-heteroaryl wherein X$^a$, q, and q$^1$ are as defined above, or
(CH$_2$)$_m$—R$^{10}$ wherein R$^{10}$ is

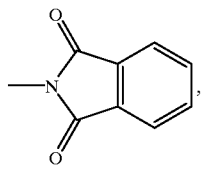

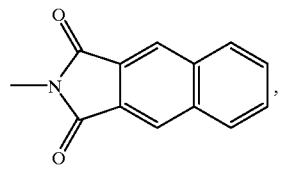

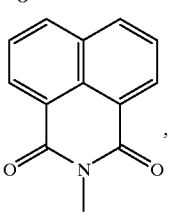

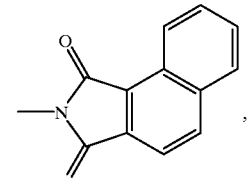

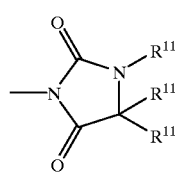

wherein R$^{11}$ is hydrogen, alkyl, aryl, arylalkyl, heteroaryl, or cycloalkyl,

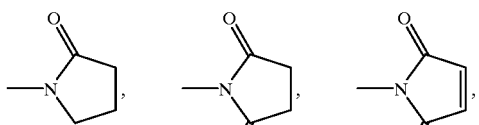

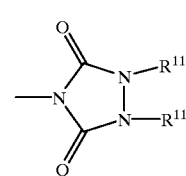

wherein R$^{11}$ is as defined above,

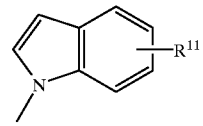

wherein R$^{11}$ is as defined above,

wherein Y is nitrogen, oxygen, sulfur, or CH$_2$ and R$^{11}$ and n are as defined above and m is as defined above, OR$^{11}$ wherein R$^{11}$ is as defined above,

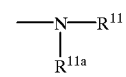

wherein R$^{11}$ and R$^{11a}$ are the sane or different and are as defined above for R$^{11}$, —SR$^{11}$ wherein R$^{11}$ is as defined above,

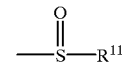

wherein R$^{11}$ is as defined above,

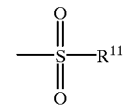

wherein R$^{11}$ is as defined above

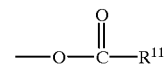

wherein $R^{11}$ is a defined above,

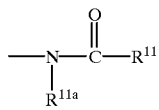

wherein $R^{11}$ and $R^{11a}$ are the same or different and are as defined above for $R^{11}$,

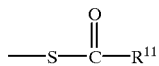

wherein $R^{11}$ is as defined above,

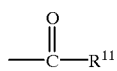

wherein $R^{11}$ is as defined above,

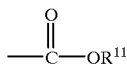

wherein $R^{11}$ is as defined above, or

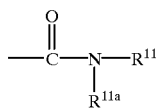

wherein $R^{11}$ and $R^{11a}$ are the same or different and are as defined above for $R^6$, or

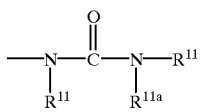

wherein $R^{11}$ and $R^{11a}$ are as defined above; and $R^5$ is OH or —NHOH;
with the proviso that when n is 1, Z is

and $R^5$ is $OR^{12}$ wherein $R^{12}$ is as defined above, then at least one of $R^1$, $R^2$, $R^3$, and $R^4$ is not hydrogen; and corresponding isomers thereof, or a pharmaceutically acceptable salt thereof.

2. The compound according to claim 1 which is

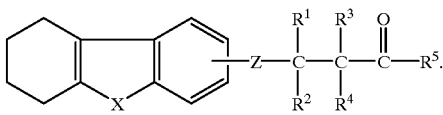

3. The compound according to claim 1 which is

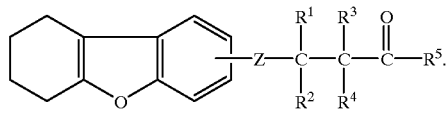

4. The compound according to claim 1 which is

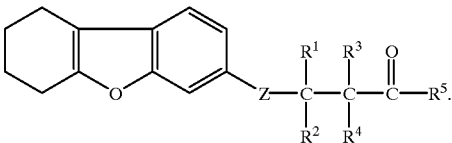

5. The compound according to claim 1 which is

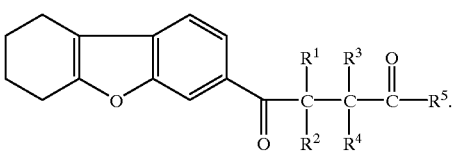

6. The compound according to claim 1 which is

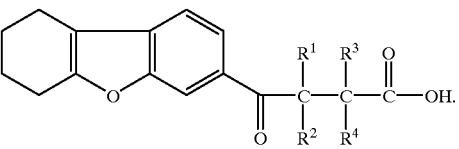

7. The compound according to claim 1 which is

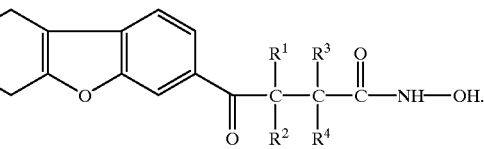

8. A compound selected from the group consisting of:
4-Hydroxyimino-4-(6,7,8,9-tetrahydro-dibenzofuran-3-yl)-butyric acid;
N-Hydroxy-4-hydroxyimino-4-(6,7,8,9-tetrahydro-dibenzofuran-3-yl)-butyramide;
N-Hydroxy-4-oxo-4-(6,7,8,9-tetrahydro-dibenzofuran-3-yl)-butyramide;
4-Oxo-2-phenethyl-4-(6,7,8,9-tetrahydro-dibenzofuran-3-yl)-butyric acid;
2-[2-Oxo-2-(6,7,8,9-tetrahydro-dibenzofuran-3-yl)-ethyl]-5-phenyl-pentanoic acid;
2-[2-Oxo-2-(6,7,8,9-tetrahydro-dibenzofuran-3-yl)-ethyl]-6-phenyl-hexanoic acid;
2-[2-Oxo-2-(6,7,8,9-tetrahydro-dibenzofuran-3-yl)-ethyl]-7-phenyl-heptanoic acid;
2-[2-Oxo-2-(6,7,8,9-tetrahydro-dibenzofuran-3-yl)-ethyl]-8-phenyl-octanoic acid;
(S) 4-Hydroxyimino-2-phenethyl-4-(6,7,8,9-tetrahydro-dibenzofuran-3-yl)-butyric acid;
(S) 2-[2-Hydroxyimino-2-(6,7,8,9-tetrahydro-dibenzofuran-3-yl)-ethyl]-5-phenyl-pentanoic acid;

(S) 2-[2-Hydroxyimino-2-(6,7,8,9-tetrahydro-dibenzofuran-3-yl)-ethyl]-6-phenyl-hexanoic acid;

(S) 2-[2-Hydroxyimino-2-(6,7,8,9-tetrahydro-dibenzofuran-3-yl)-ethyl]-7-phenyl-heptanoic acid;

(S) 2-[2-Hydroxyimino-2-(6,7,8,9-tetrahydro-dibenzofuran-3-yl)-ethyl]-8-phenyl-octanoic acid;

(S) 2-(1,3-Dioxo-1,3-dihydro-isoindol-2-ylmethyl)-4-oxo-4-(6,7,8,9-tetrahydro-dibenzofuran-3-yl)-butyric acid;

(S) 2-[2-(1,3-Dioxo-1,3-dihydro-isoindol-2-yl)-ethyl]-4-oxo-4-(6,7,8,9-tetrahydro-dibenzofuran-3-yl)-butyric acid;

(S) 5-(1,3-Dioxo-1,3-dihydro-isoindol-2-yl)-2-[2-oxo-2-(6,7,8,9-tetrahydro-dibenzofuran-3-yl)-ethyl]-pentanoic acid;

(S) 2-(1,3-Dioxo-1,3-dihydro-isoindol-2-ylmethyl)-4-hydroxyimino-4-(6,7,8,9-tetrahydro-dibenzofuran-3-yl)-butyric acid;

(S) 2-[2-(1,3-Dioxo-1,3-dihydro-isoindol-2-yl)-ethyl]-4-hydroxyimino-4-(6,7,8,9-tetrahydro-dibenzofuran-3-yl)-butyric acid;

(S) 5-(1,3-Dioxo-1,3-dihydro-isoindol-2-yl)-2-[2-hydroxyimino-2-(6,7,8,9-tetrahydro-dibenzofuran-3-yl)-ethyl]-pentanoic acid;

(S) 4-Oxo-4-(6,7,8,9-tetrahydro-dibenzofuran-3-yl)-2-(3,4,4-trimethyl-2,5-dioxo-imidazolidin-1-ylmethyl)-butyric acid;

(S) 4-Oxo-4-(6,7,8,9-tetrahydro-dibenzofuran-3-yl)-2-[2-(3,4,4-trimethyl-2,5-dioxo-imidazolidin-1-yl)-ethyl]-butyric acid;

(S) 2-[2-Oxo-2-(6,7,8,9-tetrahydro-dibenzofuran-3-yl)-ethyl]-5-(3,4,4-trimethyl-2,5-dioxo-imidazolidin-1-yl)-pentanoic acid;

(S) 4-Hydroxyimino-4-(6,7,8,9-tetrahydro-dibenzofuran-3-yl)-2-(3,4,4-triethyl-2,5-dioxo-imidazolidin-1-ylmethyl)-butyric acid;

(S) 4-Hydroxyimino-4-(6,7,8,9-tetrahydro-dibenzofuran-3-yl)-2-[2-(3,4,4-trimethyl-2,5-dioxo-imidazolidin-1-yl)-ethyl]-butyric acid;

(S) 2-[2-Hydroxyimino-2-(6,7,8,9-tetrahydro-dibenzofuran-3-yl)-ethyl]-5-(3,4,4-trimethyl-2,5-dioxo-imidazolidin-1-yl)-pentanoic acid;

4-Hydroxy-2-phenethyl-4-(6,7,8,9-tetrahydro-dibenzofuran-3-yl)-butyric acid;

2-[2-Hydroxy-2-(6,7,8,9-tetrahydro-dibenzofuran-3-yl)-ethyl]-5-phenyl-pentanoic acid;

2-[2-Hydroxy-2-(6,7,8,9-tetrahydro-dibenzofuran-3-yl)-ethyl]-6-phenyl-hexanoic acid;

2-[2-Hydroxy-2-(6,7,8,9-tetrahydro-dibenzofuran-3-yl)-ethyl]-7-phenyl-heptanoic acid;

2-[2-Hydroxy-2-(6,7,8,9-tetrahydro-dibenzofuran-3-yl)-ethyl]-8-phenyl-octanoic acid;

4-Hydroxy-4-(6,7,8,9-tetrahydro-dibenzofuran-3-yl)-2-(3,4,4-trimethyl-2,5-dioxo-imidazolidin-1-ylmethyl)-butyric acid;

4-Hydroxy-4-(6,7,8,9-tetrahydro-dibenzofuran-3-yl)-2-[2-(3,4,4-trimethyl-2,5-dioxo-imidazolidin-1-yl)-ethyl]-butyric acid;

2-[2-Hydroxy-2-(6,7,8,9-tetrahydro-dibenzofuran-3-yl)-ethyl]-5-(3,4,4-trimethyl-2,5-dioxo-imidazolidin-1-yl)-pentanoic acid;

4-Oxo-4-(6,7,8,9-tetrahydro-5H-10-oxa-benzo[a]azulen-2-yl)-butyric acid;

4-Hydroxyimino-4-(6,7,8,9-tetrahydro-5H-10-oxa-benzo[a]azulen-2-yl)-butyric acid;

(S) 4-Oxo-2-phenethyl-4-(6,7,8,9-tetrahydro-5H-10-oxa-benzo[a]azulen-2-yl)-butyric acid;

(S) 2-[2-Oxo-2-(6,7,8,9-tetrahydro-5H-10-oxa-benzo[a]azulen-2-yl)-ethyl]-5-phenyl-pentanoic acid;

(S) 2-[2-Oxo-2-(6,7,8,9-tetrahydro-5H-10-oxa-benzo[a]azulen-2-yl)-ethyl]-6-phenyl-hexanoic acid;

(S) 2-[2-Oxo-2-(6,7,8,9-tetrahydro-5H-10-oxa-benzo[a]azulen-2-yl)-ethyl]-7-phenyl-heptanoic acid;

(S) 2-[2-Oxo-2-(6,7,8,9-tetrahydro-5H-10-oxa-benzo[a]azulen-2-yl)-ethyl]-8-phenyl-octanoic acid;

(S) 4-Hydroxyimino-2-phenethyl-4-(6,7,8,9-tetrahydro-5H-10-oxa-benzo[a]azulen-2-yl)-butyric acid;

(S) 2-[2-Hydroxyimino-2-(6,7,8,9-tetrahydro-5H-10-oxa-benzo[a]azulen-2-yl)-ethyl]-5-phenyl-pentanoic acid;

(S) 2-[2-Hydroxyimino-2-(6,7,8,9-tetrahydro-5H-10-oxa-benzo[a]azulen-2-yl)-ethyl]-6-phenyl-hexanoic acid;

(S) 2-[2-Hydroxyimino-2-(6,7,8,9-tetrahydro-5H-10-oxa-benzo[a]azulen-2-yl)-ethyl]-7-phenyl-heptanoic acid;

(S) 2-[2-Hydroxyimino-2-(6,7,8,9-tetrahydro-5H-10-oxa-benzo[a]azulen-2-yl)-ethyl]-8-phenyl-octanoic acid;

4-Oxo-4-(6,7,8,9-tetrahydro-dibenzothiophen-3-yl)-butyric acid;

4-Hydroxyimino-4-(6,7,8,9-tetrahydro-dibenzothiophen-3-yl)-butyric acid;

(S) 4-Oxo-4-(6,7,8,9-tetrahydro-dibenzothiophen-3-yl)-2-(3,4,4-trimethyl-2,5-dioxo-imidazolidin-1-ylmethyl)-butyric acid;

(S) 4-Oxo-4-(6,7,8,9-tetrahydro-dibenzothiophen-3-yl)-2-[2-(3,4,4-trimethyl-2,5-dioxo-imidazolidin-1-yl)-ethyl]-butyric acid;

(S) 2-[2-Oxo-2-(6,7,8,9-tetrahydro-dibenzothiophen-3-yl)-ethyl]-5-(3,4,4-trimethyl-2,5-dioxo-imidazolidin-1-yl)-pentanoic acid;

(S) 4-Hydroxyimino-4-(6,7,8,9-tetrahydro-dibenzothiophen-3-yl)-2-(3,4,4-trimethyl-2,5-dioxo-imidazolidin-1-ylmethyl)-butyric acid;

(S) 4-Hydroxyimino-4-(6,7,8,9-tetrahydro-dibenzothiophen-3-yl)-2-[2-(3,4,4-trimethyl-2,5-dioxo-imidazolidin-1-yl)-ethyl]-butyric acid;

(S) 2-[2-Hydroxyimino-2-(6,7,8,9-tetrahydro-dibenzothiophen-3-yl)-ethyl]-5-(3,4,4-trimethyl-2,5-dioxo-imidazolidin-1-yl)-pentanoic acid;

(R) 4-Hydroxyimino-2-phenethyl-4-(6,7,8,9-tetrahydro-dibenzofuran-3-yl)-butyric acid;

(R) 2-[2-Hydroxyimino-2-(6,7,8,9-tetrahydro-dibenzofuran-3-yl)-ethyl]-5-phenyl-pentanoic acid;

(R) 2-[2-Hydroxyimino-2-(6,7,8,9-tetrahydro-dibenzofuran-3-yl)-ethyl]-6-phenyl-hexanoic acid;

(R) 2-[2-Hydroxyimino-2-(6,7,8,9-tetrahydro-dibenzofuran-3-yl)-ethyl]-7-phenyl-heptanoic acid;

(R) 2-[2-Hydroxyimino-2-(6,7,8,9-tetrahydro-dibenzofuran-3-yl)-ethyl]-8-phenyl-octanoic acid;

(R) 2-(1,3-Dioxo-1,3-dihydro-isoindol-2-ylmethyl)-4-oxo-4-(6,7,8,9-tetrahydro-dibenzofuran-3-yl)-butyric acid;

(R) 2-[2-(1,3-Dioxo-1,3-dihydro-isoindol-2-yl)-ethyl]-4-oxo-4-(6,7,8,9-tetrahydro-dibenzofuran-3-yl)-butyric acid;

(R) 5-(1,3-Dioxo-1,3-dihydro-isoindol-2-yl)-2-[2-oxo-2-(6,7,8,9-tetrahydro-dibenzofuran-3-yl)-ethyl]-pentanoic acid;

(R) 2-(1,3-Dioxo-1,3-dihydro-isoindol-2-ylmethyl)-4-hydroxyimino-4-(6,7,8,9-tetrahydro-dibenzofuran-3-yl)-butyric acid;

(R) 2-[2-(1,3-Dioxo-1,3-dihydro-isoindol-2-yl)-ethyl]-4-hydroxyimino-4-(6,7,8,9-tetrahydro-dibenzofuran-3-yl)-butyric acid;

(R) 5-(1,3-Dioxo-1,3-dihydro-isoindol-2-yl)-2-[2-hydroxyimino-2-(6,7,8,9-tetrahydro-dibenzofuran-3-yl)-ethyl]-pentanoic acid;

(R) 4-Oxo-4-(6,7,8,9-tetrahydro-dibenzofuran-3-yl)-2-(3,4,4-trimethyl-2,5-dioxo-imidazolidin-1-ylmethyl)-butyric acid;

(R) 4-Oxo-4-(6,7,8,9-tetrahydro-dibenzofuran-3-yl)-2-[2-(3,4,4-trimethyl-2,5-dioxo-imidazolidin-1-yl)-ethyl]-butyric acid;

(R) 2-[2-Oxo-2-(6,7,8,9-tetrahydro-dibenzofuran-3-yl)-ethyl]-5-(3,4,4-trimethyl-2,5-dioxo-imidazolidin-1-yl)-pentanoic acid;

(R) 4-Hydroxyimino-4-(6,7,8,9-tetrahydro-dibenzofuran-3-yl)-2-(3,4,4-trimethyl-2,5-dioxo-imidazolidin-1-ylmethyl)-butyric acid;

(R) 4-Hydroxyimino-4-(6,7,8,9-tetrahydro-dibenzofuran-3-yl)-2-[2-(3,4,4-trimethyl-2,5-dioxo-imidazolidin-1-yl)-ethyl]-butyric acid;

(R) 2-[2-Hydroxyimino-2-(6,7,8,9-tetrahydro-dibenzofuran-3-yl)-ethyl]-5-(3,4,4-trimethyl-2,5-dioxo-imidazolidin-1-yl)-pentanoic acid;

(R) 4-Oxo-2-phenethyl-4-(6,7,8,9-tetrahydro-5H-10-oxa-benzo[a]azulen-2-yl)-butyric acid;

(R) 2-[2-Oxo-2-(6,7,8,9-tetrahydro-5H-10-oxa-benzo[a]azulen-2-yl)-ethyl]-5-phenyl-pentanoic acid;

(R) 2-[2-Oxo-2-(6,7,8,9-tetrahydro-5H-10-oxa-benzo[a]azulen-2-yl)-ethyl]-6-phenyl-hexanoic acid;

(R) 2-[2-Oxo-2-(6,7,8,9-tetrahydro-5H-10-oxa-benzo[a]azulen-2-yl)-ethyl]-7-phenyl-heptanoic acid;

(R) 2-[2-Oxo-2-(6,7,8,9-tetrahydro-5H-10-oxa-benzo[a]azulen-2-yl)-ethyl]-8-phenyl-octanoic acid;

(R) 4-Hydroxyimino-2-phenethyl-4-(6,7,8,9-tetrahydro-5H-10-oxa-benzo[a]azulen-2-yl)-butyric acid;

(R) 2-[2-Hydroxyimino-2-(6,7,8,9-tetrahydro-5H-10-oxa-benzo[a]azulen-2-yl)-ethyl]-5-phenyl-pentanoic acid;

(R) 2-[2-Hydroxyimino-2-(6,7,8,9-tetrahydro-5H-10-oxa-benzo[a]azulen-2-yl)-ethyl]-6-phenyl-hexanoic acid;

(R) 2-[2-Hydroxyimino-2-(6,7,8,9-tetrahydro-5H-10-oxa-benzo[a]azulen-2-yl)-ethyl]-7-phenyl-heptanoic acid;

(R) 2-[2-Hydroxyimino-2-(6,7,8,9-tetrahydro-5H-10-oxa-benzo[a]azulen-2-yl)-ethyl]-8-phenyl-octanoic acid;

(R) 4-Oxo-4-(6,7,8,9-tetrahydro-dibenzothiophen-3-yl)-2-(3,4,4-trimethyl-2,5-dioxo-imidazolidin-1-ylmethyl)-butyric acid;

(R) 4-Oxo-4-(6,7,8,9-tetrahydro-dibenzothiophen-3-yl)-2-[2-(3,4,4-trimethyl-2,5-dioxo-imidazolidin-1-yl)-ethyl]-butyric acid;

(R) 2-[2-Oxo-2-(6,7,8,9-tetrahydro-dibenzothiophen-3-yl)-ethyl]-5-(3,4,4-7-trimethyl-2,5-dioxo-imidazolidin-1-yl)-pentanoic acid;

(R) 4-Hydroxyimino-4-(6,7,8,9-tetrahydro-dibenzothiophen-3-yl)-2-(3,4,4-trimethyl-2,5-dioxo-imidazolidin-1-ylmethyl)-butyric acid;

(R) 4-Hydroxyimino-4-(6,7,8,9-tetrahydro-dibenzothiophen-3-yl)-2-[2-(3,4,4-trimethyl-2,5-dioxo-imidazolidin-1-yl)-ethyl]-butyric acid;

(R) 2-[2-Hydroxyimino-2-(6,7,8,9-tetrahydro-dibenzothiophen-3-yl)-ethyl]-5-(3,4,4-trimethyl-2,5-dioxo-imidazolidin-1-yl)-pentanoic acid; and corresponding isomers thereof; or a pharmaceutically acceptable salt thereof.

9. The pharmaceutical composition comprising a therapeutically effective amount of a compound according to claim 1 in admixture with a pharmaceutically acceptable excipient, diluent, or carrier.

10. The method of inhibiting a matrix metalloproteinase comprising administering to a host suffering therefrom a therapeutically effective amount of a compound according to claim 1 in unit dosage form.

11. The method of inhibiting gelatinase A comprising administering to a host suffering therefrom a therapeutically effective amount of a compound according to claim 1 in unit dosage form.

12. The method of inhibiting stromelysin-1 comprising administering to a host suffering therefrom a therapeutically effective amount of a compound according to claim 1 in unit dosage form.

13. The method of inhibiting collagenase-3 comprising administering to a host suffering therefrom a therapeutically effective amount of a compound according to claim 1 in unit dosage form.

14. The method of preventing atherosclerotic plaque rupture comprising administering to a host suffering therefrom a therapeutically effective amount of a compound according to claim 1 in unit dosage form.

15. The method of inhibiting aortic aneurysm comprising administering to a host suffering therefrom a therapeutically effective amount of a compound according to claim 1 in unit dosage form.

16. The method of inhibiting heart failure comprising administering to a host suffering therefrom a therapeutically effective amount of a compound according to claim 1 in unit dosage form.

17. The method of preventing restenosis comprising administering to a host suffering therefrom a therapeutically effective amount of a compound according to claim 1 in unit dosage form.

18. The method of controlling periodontal disease comprising administering to a host suffering therefrom a therapeutically effective amount of a compound according to claim 1 in unit dosage form.

19. The method of treating corneal ulceration comprising administering to a host suffering therefrom a therapeutically effective amount of a compound according to claim 1 in unit dosage form.

20. The method of treating burns comprising administering to a host suffering therefrom a therapeutically effective amount of a compound according to claim 1 in unit dosage form.

21. The method of treating decubital ulcers comprising administering to a host suffering therefrom a therapeutically effective amount of a compound according to claim 1 in unit dosage form.

22. The method of treatment for healing wounds comprising administering to a host suffering therefrom a therapeutically effective amount of a compound according to claim 1 in unit dosage form.

23. The method of treating arthritis comprising administering to a host suffering therefrom a therapeutically effective amount of a compound according to claim 1 in unit dosage form.

24. The method of treating osteoporosis comprising administering to a host suffering therefrom a therapeutically effective amount of a compound according to claim 1 in unit dosage form.

25. The method of treating inflammation and pain comprising administering to a host suffering therefrom a therapeutically effective amount of a compound according to claim 1 in unit dosage form.

26. The method of treating renal disease comprising administering to a host suffering therefrom a therapeutically effective amount of a compound according to claim 1 in unit dosage form.

27. The method of treating left ventricular dilation comprising administering to a host suffering therefrom a therapeutically effective amount of a compound according to claim 1 in unit dosage form.

28. The pharmaceutical composition comprising a compound according to claim 1 in admixture with a pharmaceutically acceptable excipient, diluent, or carrier.

\* \* \* \* \*

UNITED STATES PATENT AND TRADEMARK OFFICE
CERTIFICATE OF CORRECTION

PATENT NO.    : 6,350,885 B1                                              Page 1 of 1
DATED         : February 26, 2002
INVENTOR(S)   : O'Brien et al.

It is certified that error appears in the above-identified patent and that said Letters Patent is hereby corrected as shown below:

Column 9,
Line 39, "heteroa" should read -- heteroaryl --

Column 51,
Line 11, "alky" should read -- alkyl --

Column 52,
Line 44, "sane" should read -- same --

Signed and Sealed this

Thirtieth Day of July, 2002

*Attest:*

*Attesting Officer*

JAMES E. ROGAN
*Director of the United States Patent and Trademark Office*